US008946189B2

(12) United States Patent
Dobson

(10) Patent No.: US 8,946,189 B2
(45) Date of Patent: Feb. 3, 2015

(54) TRANSPLANTS

(71) Applicant: Hibernation Therapeutics, A KF LLC, Camden, DE (US)

(72) Inventor: Geoffrey Phillip Dobson, Wulguru (AU)

(73) Assignee: Hibernation Therapeutics, A KF LLC, Camden, DE (US)

( * ) Notice: Subject to any disclaimer, the term of this patent is extended or adjusted under 35 U.S.C. 154(b) by 0 days.

(21) Appl. No.: 13/675,452

(22) Filed: Nov. 13, 2012

(65) Prior Publication Data

US 2013/0143833 A1 Jun. 6, 2013

Related U.S. Application Data

(63) Continuation of application No. 12/529,623, filed as application No. PCT/AU2008/000289 on Mar. 3, 2008, now abandoned.

(30) Foreign Application Priority Data

Mar. 2, 2007 (AU) .................. 2007901098

(51) Int. Cl.
*A61K 31/70* (2006.01)
*A01N 1/02* (2006.01)
*A61K 31/167* (2006.01)
*A61K 31/53* (2006.01)
*A61K 45/06* (2006.01)

(52) U.S. Cl.
CPC ............. *A01N 1/0226* (2013.01); *A01N 1/02* (2013.01); *A61K 31/167* (2013.01); *A61K 31/53* (2013.01); *A61K 45/06* (2013.01)
USPC ............................. 514/46; 514/43

(58) Field of Classification Search
USPC ....................... 514/46, 43; 435/1.1
See application file for complete search history.

(56) References Cited

U.S. PATENT DOCUMENTS

| | | | |
|---|---|---|---|
| 4,798,824 A | 1/1989 | Belzer et al. | |
| 5,006,512 A | 4/1991 | Ohnishi | |
| 5,145,771 A | 9/1992 | Lemasters et al. | |
| 5,206,222 A | 4/1993 | Forman et al. | |
| 5,256,770 A | 10/1993 | Glaser et al. | |
| 5,370,989 A | 12/1994 | Stern et al. | |
| 5,407,793 A | 4/1995 | Del Nido et al. | |
| 5,432,053 A | 7/1995 | Berdyaev et al. | |
| 5,514,536 A | 5/1996 | Taylor | |
| 5,656,420 A | 8/1997 | Chien | |
| 5,679,706 A | 10/1997 | D'Alonzo et al. | |
| 5,693,462 A | 12/1997 | Raymond | |
| 6,011,017 A | 1/2000 | Marangos et al. | |
| 6,187,756 B1 | 2/2001 | Lee et al. | |
| 6,358,208 B1 * | 3/2002 | Lang et al. | 600/438 |
| 6,372,723 B1 | 4/2002 | Martin et al. | |
| 6,569,615 B1 | 5/2003 | Thatte et al. | |
| 6,586,413 B2 | 7/2003 | Liang et al. | |
| 6,921,633 B2 | 7/2005 | Baust et al. | |
| 6,955,814 B1 | 10/2005 | Dobson | |
| 6,992,075 B2 | 1/2006 | Hill et al. | |
| 7,223,413 B2 | 5/2007 | Dobson | |
| 7,749,522 B2 | 7/2010 | Dobson | |
| 2001/0041688 A1 * | 11/2001 | Waeber et al. | 514/78 |
| 2003/0216775 A1 * | 11/2003 | Hill et al. | 606/201 |
| 2004/0056180 A1 * | 3/2004 | Yu | 250/214.1 |
| 2004/0229780 A1 | 11/2004 | Olivera | |
| 2005/0176763 A1 | 8/2005 | Boy et al. | |
| 2006/0034941 A1 | 2/2006 | Dobson | |

FOREIGN PATENT DOCUMENTS

| | | |
|---|---|---|
| CN | 1176738 A | 3/1998 |
| CN | 101019529 | 8/2007 |
| DE | 39 26287 | 2/1991 |
| GB | 2 436 255 A | 9/2007 |
| JP | 09-151134 | 6/1997 |
| SU | 0878297 | 11/1981 |
| WO | WO-92/20346 A1 | 11/1992 |
| WO | WO-98/37886 | 9/1998 |
| WO | WO-00/03716 A1 | 1/2000 |
| WO | WO-00/24378 A1 | 5/2000 |
| WO | WO-00/56145 A1 | 9/2000 |
| WO | WO-01/54679 A2 | 8/2001 |
| WO | WO-01/82914 A2 | 11/2001 |
| WO | WO-03/063782 A2 | 8/2003 |
| WO | WO-03/088978 A1 | 10/2003 |

(Continued)

OTHER PUBLICATIONS

Ar-Rajab, et al., "Improved Liver Preservation for Transplantation Due to Calcium Channel Blockade", *Transplantation*, 51(5):965-967, May 1991.

Beyersdorf, F., "The use of controlled reperfusion strategies in cardiac surgery to minimize ischaemia/reperfusion damage" *Cardiovascular Research*, 83, 262-268 (2009).

Brett, CL et al., "Evolutionary origins of eukaryotic sodium/proton exchangers" *Am J Physiol Cell Physiol*, 288, C223-C239 (2005).

Canyon, SJ, et al., "Protection Against Ventricular Arrhythmias and Cardiac Death Using Adenosine and Lidcaine During Regional Ischemia in the In Vivo Rat," *Am J. Physiol Heart Circ Physiol* 287:H1286-H1295; American Physiological Society 2004.

Canyon, SJ, et al., "Pretreatment with an Adenosine A1 Receptor Agonist and Lidocaine: A Possible Alternative to Myocardial Ischemic Preconditioning," The Journal of Thoracic and Cardiovascular Surgery, vol. 130, No. 2, pp. 371-377, 2005.

(Continued)

*Primary Examiner* — Shirley V Gembeh
(74) *Attorney, Agent, or Firm* — Venable LLP; Nancy J. Axelrod; Keith G. Haddaway

(57) ABSTRACT

The present invention relates to a method of reducing injury to cells, a tissue or organ to be explanted from a body and upon implantation into a body by administering a composition to the cell, tissue or organ, including: (i) a potassium channel opener or agonist and/or an adenosine receptor agonist; and (ii) an antiarrhythmic agent. The invention also provides a composition for reducing injury to vasculature ex vivo including: (i) a potassium channel opener or agonist and/or an adenosine receptor agonist; and (ii) an antiarrhythmic agent.

17 Claims, 3 Drawing Sheets

(56) References Cited

FOREIGN PATENT DOCUMENTS

Figure 1:
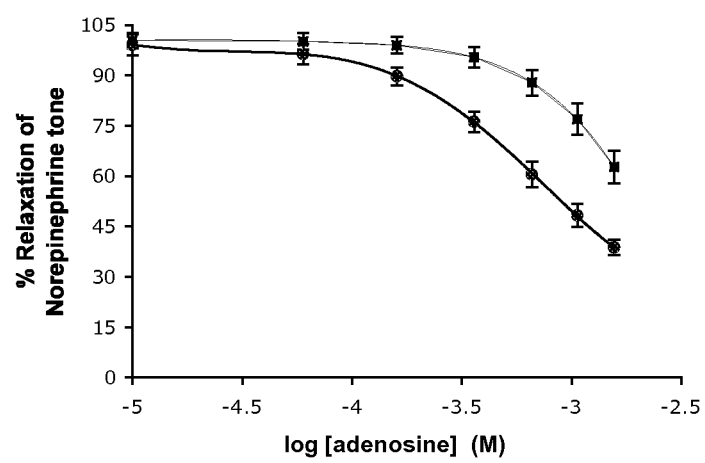

| WO | WO-04/000331 A1 | 12/2003 |
| --- | --- | --- |
| WO | WO-2004/056180 A1 | 7/2004 |
| WO | WO-2004/056181 A1 | 7/2004 |
| WO | WO-2004/060286 A2 | 7/2004 |
| WO | WO-2004/108666 A2 | 12/2004 |
| WO | WO-2006/069170 A2 | 6/2006 |
| WO | WO-2007/030198 A2 | 3/2007 |
| WO | WO-2007/137321 A1 | 12/2007 |
| WO | WO-2008/011670 A1 | 1/2008 |
| WO | WO-2008/106724 A1 | 9/2008 |
| WO | WO-2009/012534 A1 | 1/2009 |

OTHER PUBLICATIONS

Canyon, SJ, et al., "The Effect of Adenosine and Lidocaine Infusion on Myocardial High-Energy Phosphates and pH During Regional Ischemia in the Rat Model in vivo", Canadian Journal of Physiology and Pharmacology, vol. 84, 903-912, Oct. 18, 2006.

Chien, S, et al., "Extension of Tissue Survival Time in Multiorgan Block Preparation With a Delta Opioid DADLE(D-Ala2, D-Leu5)-enkephalin)," The Journal of Thoracic and Cardiovascular Surgery, 107:965967, 1994.

Corvera, JS, et al., "Polarised Arrest With Warm or Cold Adenosine/Lidocaine Blood Cardioplegia is Equivalent to Hypothermic Potassium Blood Cardioplegia," The Journal of Thoracic and Cardiovascular Surgery, 129(3):599-606, May 2005.

Das, et al., "Myocardial preservation during cardiac surgery", Annals of Cardiac Anaesthesia, vol. 5, pp. 25-32, 2002.

Dobson, G.P., "Organ Arrest, Protection and Preservation: Natural Hibernation to Cardiac Surgery," Comparative Biochemistry and Physiology, 139 (Part B):469-485; Elsevier Inc., 2004.

Dobson, G.P., et al., "Adenosine and Lidocaine: A New Concept in Nondepolarizing Surgical Myocardial Arrest, Protection and Preservation," The Journal of Thoracic and Cardiovascular Surgery 127:794-805, Mar. 2004.

Ely, S.W., et al., "Protective Effects of Adenosine in Myocardial Ischemia", Circulation, 85(3): 893-904, Mar. 1992.

Forman, et al., "Mechanisms and Therapy of Myocardial Reperfusion Injury". Circulation, 81(3 Suppl):IV69-78, Mar. 1990.

Forman, et al., "Adenosine Therapy at Reperfusion on Myocardial Infarct Size," Cardiovascular Research, 33:497-498, 1997.

Garratt, et al., "Intravenous Adenosine and Lidocaine in Patients with Acute Myocardial Infarction," American Heart Journal, 136(2): 196-204, Aug. 1998.

Goto, et al., "Adenosine Infusion During Early Reperfusion Failed to Limit Myocardial Infarct Size in a Collateral Deficient Species" Cardiovascular Research, 25(11):943-9, Nov. 1991.

Granger, C.B., "Adenosine for Myocardial Protection in Acute Myocardial Infarction", The American Journal of Cardiology, 79(12A): 44-48, Jun. 1997.

Hearse, et al., "Protection of the Myocardium during ischemic arrest," J. Thorac. Cardiovasc. Surg., vol. 81, No. 6, pp. 873-879, 1981.

Hicks, et al., "ATP-Sensitive Potassium Channel Activiation Mimics the Protective Effect of Ischaemic Preconditioning in the Rat Isolated Working Heart After Prolonged Hypothermic Storage," Clinical and Experimental Pharmacology and Physiology 26:20-25, 1999.

Homeister, et al., "Combined Adenosine and Lidocaine Administration Limits Myocardial Reperfusion Injury," Circulation, 82(2):595-608, Aug. 1990.

Huang, T.F., "Drug Effects on the Ischemia- and Reperfusion-induced Arrhythmias in the Conscious Rats", Chinese Journal of Physiology 35(1): 9-19,1992.

International Preliminary Examination Report, dated Mar. 5, 2001, issued in related International Application No. PCT/AU00/00226.

International Preliminary Examination Report, dated Oct. 12, 2004, issued in related International Application No. PCT/AU2003/000771.

International Preliminary Report on Patentability, dated Dec. 3, 2008, issued in related Internatibnal Application No. PCT/AU2006/000717.

International Preliminary Report on Patentability, dated Jan. 27, 2009, issued in related International Application No. PCT/AU2007/001029.

International Preliminary Report on Patentability, dated Sep. 8, 2009, issued in related International Application No. PCT/AU2008/000289.

International Preliminary Report on Patentability, dated Jan. 26, 2010, issued in related International Application No. PCT/AU2008/001086.

International Search Report dated Jun. 9, 2000, issued in related International Application No. PCT/AU00/00226.

International Search Report dated Aug. 4, 2003, issued in related International Application No. PCT/AU03/00771.

International Search Report dated Feb. 13, 2004, issued in related International Application No. PCT/AU2003/001710.

International Search Report dated Feb. 13, 2004, issued in related International Application No. PCT/AU2003/001711.

International Search Report dated Jul. 21, 2006, issued in related International Application No. PCT/AU2006/000717.

International Status Report, Dated Sep. 25, 2007, issued in related International Application No. PCT/AU2007/001029.

International Search Report, dated May 7, 2008, issued in related International Application No. PCT/AU2008/000289.

International Search Report dated Sep. 25, 2008, issued in related International Application No. PCT/AU2008/001086.

Jakosben, et al., "Adenosine instead of supranormal potassium in cardioplegic solution improves cardioprotection," European Journal of Cardio-thoracic Surgery, vol. 32, pp. 493-500, 2007.

Jakosben, et al., "Adenosine instead of supranormal potassium in cardioplegic solution preserves endothelium-derived hyperpolarization factor-dependent vasodilation", European Journal of Cardio-thoracic Surgery, vol. 33, pp. 18-24, 2008.

Jayawant, et al., "Advantages of Continuous Hyperpolarized Arrest with Pinacidil Over St. Thomas' Hospital Solution During Prolonged lschemia," J. Thoracic and Cardiovascular Surgery, 11(1): 131-138, 1998.

Jayawant, AM et al "Potassium-channel opener cardioplegia is superior to St. Thomas' solution in the intact animal" Ann Thorac Surg, 68, 67-74 (1999).

Jin, et al, "The myocardial protective effects of a moderate-potassium adenosine-lidocaine cardioplegia in pediatric cardiac surgery", The Journal of Thoracic and Cardiovascular Surgery, vol. 136, No. 6, pp. 1450-1455, 2008.

Karck, M., et al, "Myocardial protection by ischemic preconditioning and -opioid receptor activiation in the isolated working rat heart" The Journal of Thoracic and Cardiovascular Surgery, 122, 986-992 (2001).

Kinoshita, H., et al "Mild alkalinisation and acidification deifferentially modify the effects of lidocaine or mexiletine on vasorelaxation mediated by ATP-sensitive K+ channels" Anesthesiology, 95, 200-206 (2001).

Kusano T. et al., "Organ Preserving Effect of lidocaine Administration in the Model of Orthopic Liver Transplantation from Non-heart Beating Donors", Transplantation Proceedings, 28(3): 1928-1929, Jun. 1996.

Lee et al., "Retrograde infusion of liocaine or L-arginine before reperfusion reduces myocardial infarct size", Ann. Thorac. Surg 65:1353-1359, 1998.

Mahaffey, et al., "Adenosine as an Adjunct to Thrombolytic Therapy for Acute Myocardial Infarction," JACC 34(6): 1711-20, Nov. 1999.

Neely, et al., "A1 Adenosine Receptor Antagonist Block Ischemia-reperfusion Injury of the Heart", Circulation, Supplement 94(9):11376-11380, 1996, abstract.

O'Rullian, et al., "Excellent Outcomes in a Case of complex Re-do Surgery Requiring Prolonged Cardioplegia Using a New Cardioprotective Approach: Adenocaine," The Journal of ExtraCorporeal Technology, vol. 40, pp. 203-205, 2008.

(56) References Cited

OTHER PUBLICATIONS

Rogriguez-Reynoso, et al "Effect of exogenous melatonin on hepatic energetic status during ischemia/reperfusion: possible role of tumor necrosis factor-a and nitric oxide" *J Surgical Research*, 100(2), 141-149 (2001).

Rudd, DM, et al. "Toward a New Cold and Warm Nondepolarizing, Normokalemic Arrest Paradigm for Orthotopic Heart Transplantation", Journal of Thoracic and Cardiovascular Surgery, 137(1): 198-207, Jan. 2009.

Schubert, et al., "Adenosine cardioplegia," J. Thorac. Cardiovasc. Surg., vol. 98, No. 6, pp. 1057-1065, 1989.

Segal, et al., "On the Natriuretic Effect of Verapamil: Inhibition of EnaC and Transephithelial Sodium Transport", Am J. Physiol Renal Physiol, 283: F765-F770, 2002.

Sigg, et al "Role of d-opioid receptor agonists on infarct size reduction in swine" Am. J. Physiol. Heart Circ. Physiol, 282, H1953-H1960 (2002).

Silber, et al "A rapid hemodynamic monitor of acute ischemia during cardiac procedures: changes in relaxation via a continuous left ventricular pressure-derivative loop" J Surg Res, 134(1), 107-113 (2006) with Medline entry Acc No. 2006367738.

Sloots, K, et al, "Warm nondepolarizing adenosine and lidocaine cardioplegia: Continuous versus intermittent delivery," The Journal of Thoracic and Cardiovascular Surgery, vol. 133, No. 5, pp. 1171-1178. 2007.

Su, T-P., "Delta Opioid Peptide [D-Ala2, D-Leu5] Enkephalin Promotes Cell Survival," J. Biomed. Sci., 7:195-199, 2000.

Sultan, et al., "Heart Preservation: Analysis of Cardioprotective Infusate Characteristics, Membrane Stabilization, Calcium Antagonism, and Protease Inhibition on Myocardial Viability: A Biochemical, Ultrastructural, Functional Study," The Journal of Heart and Lung Transplantation 11(4):607-18, 1992.

Takeuchi, et al. "Prolonged Preservation of the Blood-Perfused Canine Heart with Glycolysis-Promoting Solution," Ann Thorac Surgery 68:903-7, 1999.

Ulusal, et al., "The Effect of A2a Adenosine Receptor Agonist on Composite Tissue Allotransplant Survival: An In Vitro Preliminary Study", J. Surgical Research 131: 261-266, 2006.

Vander Heide, et al., "Adenosine Therapy at Reperfusion and Myocardial Infarct Size," Cardiovascular Research, 33:499-500, 1997.

Vinten-Johansen, J., et al. "Preconditioning and postconditioning: innate cardioprotection from ischemia-reperfusion injury." Journal of Applied Physiology, 103(4). pp. 1441-1448, 2007.

Wu, et al., "Mechanism of cardiac protection by preconditioning and postconditioning for hypoxia-reoxygenation injury is different" Jpn J Physiol, 54, S96, item 127 (2004).

\* cited by examiner

TRANSPLANTS

This application is a continuation application of U.S. patent application Ser. No. 12/529,623, filed Sep. 2, 2009, which is a national stage application of PCT/AU2008/000289, which was filed on Mar. 3, 2008.

FIELD OF THE INVENTION

This invention relates to a method of protecting cells, a tissue or organ of a body, particularly during surgery. It has particular but not exclusive application in the context of coronary artery bypass graft surgery in protecting a blood vessel during harvesting, testing and storage as well as implantation of the graft and its patency.

BACKGROUND OF THE INVENTION

Pioneering work in the surgical technique of anastomosis of arteries and veins was made in the early 1900s by the French surgeon Alexis Carrel (1873-1944). From Carrel's careful methods of protecting the vessels during harvest and storage and delicate anastomosis operations he laid the groundwork for the development of vascular surgery and transplantation. In 1912, Carrel wrote: "In operations on blood-vessels certain general rules must be followed. These rules have been adopted with the view of eliminating the complications which are especially liable to occur after vascular sutures, namely, stenosis, haemorrhage, and thrombosis." One such rule was to carefully wash the vessel with Ringer's solution and coat it and the surrounding parts of the operating-field with Vaseline to protect the endothelium against "coagulating blood and the juices of tissues". Carrel knew that damage to the vascular endothelium, the largest organ of the body, led to injury, thrombus and poor outcomes.

One hundred years later, despite major advances in vascular biology and pathobiology, surgeons are still debating the best way to harvest, store and transplant arterial or venous grafts for vascular or cardiac surgery. Globally there are over 800,000 patients who undergo coronary artery bypass graft (CABG) surgery each year, with more than 350,000 patients in the US. On average there are three grafts per operation or about 2.4 million anastomoses performed globally each year, or about 1.0 million in the USA. With the current technology, the current patency rate of arterialisation saphenous vein (SV) grafts following CABG is 80% in the first year, and the patency at 10 years is around 60% compared to 85% for the left internal mammary (LIMA) grafts to the left anterior descending coronary artery (LAD). Thus, an ongoing problem is the early graft occlusion rate of 20% in the first year.

The reasons for a high occlusion rate in the first year may involve vessel damage, including endothelial damage and alterations in vascular reactivity of the vessel, which may have occurred during: 1) the graft harvest (blunt surgical trauma), 2) stretching the vessel, 3) high pressure testing, 4) storage of the graft 5) surgical attachment, 6) temperature fluctuations, and 7) ischemia-reperfusion injury during restoration of blood flow following the anastomoses and/or during reanimation before removing the patient off bypass. In addition, the allograft graft vessels may have different pre-existing pathologies and wall thicknesses (e.g atherosclerosis, fibrosis, post inflammatory changes, various degrees of varicosis etc), which would impact on the vulnerability to injury and stability of the graft.

A particular area of concern with current technologies is the storage procedure and time between harvest and surgical attachment (or re-implantation), which may for example extend to 5 hours or longer during a CABG operation. The storage procedure includes placing the harvested vessel conduit in a solution which may be a patient's heparinized blood, tissue culture medium, Hanks solution or a crystalloid solution including hyperkalemic cardioplegia. Particular attention must be paid to the storage temperature of the solution which may effect the extent and duration of graft ischemia during harvest and during surgical attachment. In more difficult operations and on older patients, surgeries and storage times may be up to 5 hours before re-implantation.

One of the key strategies in the protection and preservation of the transplant is to prevent the vascular endothelium from becoming injured or activated and to preserve endothelium-smooth muscle interactions. An injured or activated endothelium loses many of its homeostatic or balancing functions and becomes proinflammatory and prothrombolytic, prooxidant, profibrinolytic and proathrogenic. Thus past methodologies have aimed to reduce graft reactivity, patency and early failure by preserving the functional integrity of the vascular endothelium and its interactions between the blood or bathing solution and the smooth muscle layer of the vessel wall. However, no therapy has proven to be clinically successful as evidenced by the high 20% patency failure in the first year. For example, one troubling and continuing problem with harvested and transplanted grafts for CABG and vascular surgery is vasospasm. Vasospasm is defined as an exaggerated hypercontractile response or state of a vessel's smooth muscle to various stimuli which may be precipitated by endothelial dysfunction, shear stresses, smooth muscle calcium hypersensitivity, increased autonomic tone (parasympathetic and alpha-adrenergic receptors) and increased oxidative stress.

In the past 10 years, vasospasm has become particularly challenging with a resurgence of use of the radial artery graft after it was abandoned in the mid-1970s because of a high incidence of vasospasm and a 35% failure rate at 2 years. Arterial grafts are known to have inherent spasticity compared to saphenous veins, because of a thicker layer of smooth muscle and connective tissue, and different endothelial-smooth muscle functions. Arterial grafts possess more pronounced endothelium-dependent relaxation properties to acetylcholine, bradykinin, histamine, substance P and mechanical sheer stress than saphenous veins. In addition, cooling has shown to act as a vasodilator in human internal thoracic arteries, saphenous veins, aorta, coronary arteries, and pulmonary arteries.

It is not known whether protection could be elicited by a form of artificial hibernation-like state for the graft. Natural hibernators possess the ability to lower their metabolic energy demand for days to months. Hibernation, like sleep, is a form of dormancy and helps to keep the animal's metabolic supply and demand ratio in balance. WO00/56145 (U.S. Pat. No. 6,955,814), WO04/056180 and WO04/056181 describe compositions useful to limit damage to a cell, tissue or organ by administering them to a patient in a clinical setting. Selective administration of adenosine A2A receptors has also been proposed in U.S. Pat. No. 6,372,723.

SUMMARY OF THE INVENTION

The present invention is directed toward overcoming or at least alleviating one or more of the difficulties and deficiencies of the prior art.

In one aspect the present invention is directed to a method of reducing injury to cells, a tissue or organ to be explanted from a body and upon implantation into a body by administering a composition to the cell, tissue or organ, including:

(i) a potassium channel opener or agonist and/or an adenosine receptor agonist; and
(ii) antiarrhythmic agent.

In another embodiment, the invention is directed to a method of improving recovery of cells, a tissue or organ upon implantation into a body by administering a composition including:
(i) a potassium channel opener or agonist and/or an adenosine receptor agonist; and
(ii) antiarrhythmic agent.

Preferably, the composition includes (i) and (ii) in amounts effective to arrest the heart, as described below.

Preferably, the composition according to this aspect may further include at least one muscle relaxant. The muscle relaxant may be selected from the group consisting of botulinum toxin (e.g. botox), myosin light chain kinase inhibitor, calmodulin blocker, calcium channel blocker, nitric oxide donor, dipyridamole, beta blocker, Na/H inhibitor, high magnesium, opioid, phosphodiesterase inhibitors (eg. papaverine, milrinone, theophylline, dipyridamole, alpha-adrenergic receptor antagonists (phenoxybenzamine) and Rho kinase inhibitors (eg HA1077 or fausdil).

According to this aspect of the invention, the composition may be administered directly to the cells, tissues or organs that are intended to be explanted, or to cells, tissue or organs that have been explanted or to cells, tissues or organs that have been implanted, or administered at a combination of these stages of explanation and implantation. In addition, the composition may be administered in a non-arresting concentration to a patient following surgery.

Preferably, the composition is pre-mixed with the patient's blood.

Preferably, the cell, tissue or organ is a blood vessel, such as a saphenous vein.

In another aspect the present invention provides a composition for reducing injury to vasculature ex vivo including:
(i) a potassium channel opener or agonist and/or an adenosine receptor agonist; and
(ii) antiarrhythmic agent.

DETAILED DESCRIPTION

In one form, the invention provides a method of reducing injury to cells, a tissue or organ removed or explanted from the body comprising administering a composition including: (i) a potassium channel opener or agonist and/or an adenosine receptor agonist; and (ii) an antiarrhythmic agent. In one embodiment, the composition includes (i) a potassium channel opener or agonist and/or an adenosine receptor agonist; and (ii) an antiarrhythmic agent, in amounts below that effective to arrest a heart, as described below. In an alternative embodiment, the composition includes (i) a potassium channel opener or agonist and/or an adenosine receptor agonist; and (ii) an antiarrhythmic agent in amounts effective to arrest the heart. In the present application, an amount effective to arrest the heart is an amount in a composition that contacts causes the heart of a rat to arrest upon contact. These amounts necessary to arrest a heart are readily determinable for a given selection of a potassium channel opener or agonist and/or an adenosine receptor agonist, and a given antiarrhythmic agent. For example, if adenosine and lidocaine are the selected compounds to arrest the heart, concentrations above 0.1 mM (and preferably below 20 mM) for each in the composition that contacts the heart are effective to arrest the heart. In this specification, higher and lower amounts of these components are referred to as arresting and non-arresting compositions respectively. This is further explained below.

The composition of the invention desirably reduces, at least in part, reperfusion injury. As outlined above, reperfusion injury is a common deleterious occurrence upon completion of a procedure. In this embodiment, the composition may be administered as a composition ex vivo, as a non-arresting bolus injection or delivered continuously via an intravenous drip or by another delivery device or route. In one form, the present invention is used ex vivo at high arresting concentrations and then in vivo (for example, following a surgical operation) using a (lower) non-arresting concentration.

In another embodiment, the invention provides a method of keeping the membrane voltage of the cells close to or near their resting or natural state. Voltage balance is believed to be important to promote a healthy vessel wall, including the integrity of the smooth muscle and endothelium.

Without being bound by any theory or mode of action, the inventor has found that the composition according to the invention can be used to place cells, tissue and organs, in effect, toward a state of suspended animation like a natural hibernator or to stabilise the cells, a tissue or organ. The overall protection provided by therapy according to the invention is thought to involve a multi-tiered system from modulating membrane excitability to a multitude of intracellular signalling pathways, including heat shock and pro-survival kinase pathways. Non-binding theories of proposed mechanisms of the composition of the invention include (i) reduced wide swings in cell membrane voltage and ion imbalances, in particular sodium and calcium ion loading in the cells, which may help defend the cell's voltage when stressed; (ii) attenuation of local and systemic inflammatory response to injury, which is protective in itself to reduce injury as well as reduce secondary effects such as free radical production; and (iii) protection from entering into a hypercoagulable state, ie an anti-clotting or anti-thrombolytic activity. Thus the present invention is trying to maintain the vessel in homeostatic balance in the physiological ranges representative of the uninjured state which includes but it not limited to keeping smooth muscle relaxed and the endothelium from becoming proinflammatory, prothrombolytic, prooxidant, profibrinolytic and proathrogenic. It is also believed that the composition may reduce the cell, organ, tissue and body's demand for oxygen to varying degrees and thus reduce damage to the body's cells, tissues or organs.

Damage may be caused to an organ such as a heart or a blood vessel upon reperfusion. Damage may be caused to the vessel itself, and also to its endothelium, upon harvesting. Once harvested, pressure testing of the vessel, often involving substantial stretching of the outer, medial and inner layers including the endothelium, can cause damage. Finally, the transplanting or implanting of the vessel and restoring flow requires substantial impact on all three layers including the endothelium. Minimising damage to these layers including the endothelium is desirable because during injury the endothelium becomes activated and dramatically alters its phenotype to become pro-inflammatory, pro-coagulant and pro-thrombotic, pro-oxidant and pro-athrogenic. Five major changes that can lead to impaired vessel reactivity, spasm and loss of patency are: 1) platelet adhesion, platelet aggregation and platelet activation at the site of injury. Activation of the endothelium leads to growth factor releases and cytokines (Cytokine 1, 6 & 8), P selection which in turn activates leukocytes. Platelet activation also leads to tissue factor generation and thrombin and contributes to thrombus generation and clot formation, 2) leukocyte activation is the hallmark of the inflammatory process in response to endothelial injury-recruitment and vessel wall invasion is driven by cytokines and chemokines, inflammation to the outer adventitia layer of the vessel also plays a role, 3) activation of the coagulation cascade and thrombin generation arises from endothelial injury and exposure of tissue factor in the vessel wall to the circulating blood. Inhibiting tissue factor markedly reduces the thrombogenic response to injury, and therefore intimal hyperplasia, 4) smooth muscle cells in the medial layer migrate as a result of growth factors, cytokines, extracellular matrix proteins and cell surface receptors, and 5) smooth muscle cells begin to proliferate which leads to the narrowing of the vessel's lumen. In rat vascular tissue, for example, the percentage of dividing smooth muscle cells increases from a basal 0.06% to 10-30% (a 500 fold increase) per day following a vascular insult. The magnitude of the inflammatory and thrombotic responses and vessel reactivity and therefore patency depends on the severity of the injury and the degree of subendothelial exposure. These events are just the opposite of what is required in an implanted vessel.

Damage to the graft itself can be exacerbated by the presence of depolarising potassium in cardioplegia as depolarising potassium is a known and potent vasoconstrictor of isolated vessels, which causes the grafts to constrict, often leading to spasm, and then possibly further damage and to loss of patency/closure. A particularly vulnerable time is when the grafted vessel is first reperfused with a cardioplegic solution and the temperature of that reperfusion and during reanimation. In this way, the invention seeks to reduce or avoid the use of depolarising potassium used during these cardiac surgical procedures for cardioplegic induction, maintenance and reanimation.

In addition to the critical "window" between harvest, storage and surgical implantation, which may extend to 5 hours, another equally critical "window" for the protection and preservation of the transplanted graft is the first 6 months following the surgery. When a vessel is damaged during harvest, storage and surgical implantation, these effects can lead remodelling of the injured layers including intimal proliferation following surgery and thereby reduced patency and possibly graft failure. Thus there are two windows of opportunity. Damage to the vessel during the first window can profoundly influence the outcome in the weeks to months following surgery.

In one form, the invention provides a method for reducing electrical disturbance of a cell, tissue or organ comprising administering an effective amount of a composition comprising an effective amount of (i) a potassium channel opener or agonist and/or an adenosine receptor agonist; and (ii) an antiarrhythmic agent, and of one or more of an anti-adrenergic, a calcium antagonist, an opioid, an NO donor, a sodium hydrogen exchange inhibitor and a muscle relaxant (particularly a smooth muscle relaxant). Also provided is a method for reducing damage to an organ or tissue following ischaemia comprising administering an effective amount of a composition comprising an effective amount of a local anaesthetic and of one or more of a potassium channel opener, an adenosine receptor agonist, an anti-adrenergic, a calcium antagonist, an opioid, an NO donor, a sodium hydrogen exchange inhibitor and a smooth muscle relaxant.

The invention also provides a method for preconditioning a tissue or organ prior to ischaemia or reperfusion comprising administering an effective amount of a composition comprising an effective amount of (i) a potassium channel opener or agonist and/or an adenosine receptor agonist; and (ii) an antiarrhythmic agent and of one or more of an anti-adrenergic, a calcium antagonist, an opioid, an NO donor, a sodium hydrogen exchange inhibitor and a smooth muscle relaxant.

The invention also provides a method for reducing inflammation in a tissue or organ comprising administering an effective amount of a composition comprising an effective amount of (i) a potassium channel opener or agonist and/or an adenosine receptor agonist; and (ii) an antiarrhythmic agent and of one or more of an anti-adrenergic, a calcium antagonist, an opioid, an NO donor, a sodium hydrogen exchange inhibitor and a smooth muscle relaxant.

The invention may also be used to provide a method for reducing damage to cells, organs and tissues before, during and following surgery comprising administering an effective amount of a composition comprising an effective amount of (i) a potassium channel opener or agonist and/or an adenosine receptor agonist; and (ii) an antiarrhythmic agent and of one or more of an anti-adrenergic, a calcium antagonist, an opioid, an NO donor, a sodium hydrogen exchange inhibitor and a smooth muscle relaxant.

The invention is in one embodiment particularly directed to improved methods for preserving transplant grafts ex vivo, such as vasculature grafts. In particular, the invention is directed to protecting grafts during harvesting. It is also directed to protecting grafts during storage pending implantation (which may be for a quite short period or a period of hours or longer). It is also directed to protecting grafts during pressure testing, or other testing, of the graft prior to implantation (eg inflation of the graft in the presence of a composition of the invention). The invention is also directed to reducing damage to grafts upon implantation and recovery. The invention may be used at each of these steps. It is believed that this is achieved by reducing the degree of constriction of the grafts, and consequential reduced vessel wall and endothelial damage, as well as providing a non-depolarising potassium environment for implantation (closer to normal physiological levels). The invention is also directed to reducing the patency failure rate post-operatively of those grafts, thus providing longer-term success of bypass procedures. This can be achieved by relaxing the vasculature smooth muscle using a composition of the invention, and optionally further including long-acting smooth muscle relaxants to the grafts prior to and/or upon implantation. Thus, in one aspect of the invention, the composition reduces the energy demand of the vessel including the smooth muscle layer by placing it in a hibernating-like state.

A major difference between a composition of the invention (such as a composition which includes (i) a potassium channel opener or agonist and/or an adenosine receptor agonist; and (ii) an antiarrhythmic agent) compared with adenosine alone is that the relaxation profile is not dependent on an intact endothelium (as it is with adenosine). The effect of the invention on denuded vasculature rings is as if the endothelium had not been removed. One clinical significance of this surprising result is improved storage of a subject's harvested conduit arteries or veins for prepared for bypass surgery (or other vascular surgery) which are known to suffer varying degrees of endothelial damage. During dissection, storage or anastomoses, the luminal endothelial layer, the outer adventitial layer and the medial smooth muscle layer are vulnerable to damage and spasm (uncontrolled contraction). The invention protects the vessel wall including the endothelium and relaxes vascular smooth muscle and thereby reducing vascular spasms during vessel dissection, storage or anastomoses. It can also provide better protection against short-term and long-term restenosis. The mechanism of action as to how greater relaxation occurs in the presence of a composition according to the invention, such as adenosine and lidocaine, over the summed effects of adenosine alone and lidocaine alone has not been fully determined.

Accordingly, the present invention provides a method of reducing injury to cells, a tissue or organ to be removed or explanted from a body, upon implantation into a body and during recovery in a body by administering a composition to the cells, tissue or organ, including (i) a potassium channel opener or agonist and/or an adenosine receptor agonist; and (ii) an antiarrhythmic agent, where the endothelium of the tissue or organ is damaged or is non-functional.

The invention applies to protecting, preserving or stabilising key organs or tissue ex vivo. In one embodiment, the organ or tissue is blood vessels, such as those used a grafts in a cardiac pulmonary bypass procedure.

In another form, the invention provides a composition for protecting cells, tissues or organs to be removed, the composition including (i) a potassium channel opener or agonist and/or an adenosine receptor agonist; and (ii) an antiarrhythmic agent. Analogous to the theory explained above, it is believed that the composition reduces metabolic activity of the tissue, thus reducing its susceptibility to damage (for example, ischaemic damage) upon surgical excision. The composition may be administered systemically or at the site of surgery to the cell, tissue or organ, and the explanted cell, tissue or organ may then be maintained in a bath of, or having a continuous supply, of a composition according to the invention. In addition, the composition may be added to the fluid used to test explanted tissue (for example, pressure testing) to reduce damage during those processes. In a preferred form, the tissue is a blood vessel, such as a saphenous vein.

In another form, the composition of the invention is administered upon implant of a cell, tissue or organ. It is believed, again without being bound by any theory or mode of action, that the composition reduces undesirable vasoconstriction and/or inflammation and/or thrombolytic responses, which may otherwise arise from the implantation.

The invention also provides a method of reducing damage to a cell, tissue or organ which is to be explanted, has been explanted and has been implanted, or more than one of these. In particular, the invention has application to the harvesting, storage and grafting of vasculature, the method including the administration of a composition of the invention as described herein. The invention includes bathing explanted cells, tissue or organs in a composition including the composition of the invention. In one form suitable for all stages of the method described above, the composition of the invention is premixed with the patient's blood (at, for example, 1 mM concentration) for use.

For example, a patient may be administered the composition of the invention prior to harvesting of a tissue, such as a blood vessel, to reduce the susceptibility of the vessel to injury from the inherently damaging process of excision. The excised tissue is then immediately placed in a bath of a composition that includes primarily the patient's blood, together with a composition of the invention (for example, adenosine and lignocaine). This combination fluid is also suitable for testing the explanted tissue. The invention includes administering additional composition of the invention upon grafting or implantation of the cell, tissue or organ. This can assist in reducing reperfusion injury, as well as reducing the inflammatory and thrombotic responses which may otherwise be triggered upon implantation of the cell, tissue or organ.

In another form, the invention provides for use of (i) a potassium channel opener or agonist and/or an adenosine receptor agonist; and (ii) an antiarrhythmic agent in the manufacture of a medicament for administration to a patient, or to cells, a tissue or organ removed from a body of the patient, to reduce injury or damage as discussed above.

In various forms, the invention may further include one or more of a muscle relaxant which could be chosen from a list of compounds that act either presynaptically, at the nerve-muscle junction, post-synaptically or directly act on or within smooth muscle itself which results in relaxation, such as vasodilation. Some muscle relaxants include a botulinum toxin (e.g. botox), myosin light chain kinase inhibitor, calmodulin blocker, calcium channel blocker, nitric oxide donor, dipyridamole, beta blocker, Na/H inhibitor, high magnesium, opioid, phosphodiesterase inhibitors (eg. papaverine, milrinone, theophylline, dipyridamole, alpha-adrenergic receptor antagonists (phenoxybenzamine) and Rho kinase inhibitors (eg HA1077 or fausdil).

The compositions as described above in various embodiments of the invention may further include other components as identified below. In some embodiments, the potassium channel opener or agonist and/or adenosine receptor agonist is replaced by another component such as a calcium channel blocker. The composition preferably contains an effect amount of (i) and (ii) for a single dose to reduce injury.

In the embodiments of the invention described above and below, component (i) of the composition may be an adenosine receptor agonist. While this obviously includes adenosine itself, the "adenosine receptor agonist" may be replaced or supplemented by a compound that has the effect of raising endogenous adenosine levels. This may be particularly desirable where the compound raises endogenous adenosine levels in a local environment within a body. The effect of raising endogenous adenosine may be achieved by a compound that inhibits cellular transport of adenosine and therefore removal from circulation or otherwise slows its metabolism and effectively extends its half-life (for example, dipyridamole) and/or a compound that stimulates endogenous adenosine production such as purine nucleoside analogue Acadesine™ or AICA-riboside (5-amino-4-imidazole carboxamide ribonucleoside)). Acadesine is also a competitive inhibitor of adenosine deaminase (Ki=362 microMolar in calf intestinal mucosa. Acadesine™ is desirably administered to produce a plasma concentration of around 50 microM (uM) but may range from 1 microM to 1 mM or more preferably from 20 to 200 uM. Acadesine™ has shown to be safe in humans from doses given orally and/or intravenous administration at 10, 25, 50, and 100 mg/kg body weight doses.

In one form of the invention, the composition, and optionally the second composition, also contains magnesium cations. In one embodiment, the concentration of magnesium is up to about 2.5 mM and in another embodiment magnesium is present in higher concentrations, for example up to about 20 mM. The magnesium is present as a physiologically and pharmaceutically acceptable salt, such as for example magnesium chloride and magnesium sulphate.

The invention described in this specification largely relates to methods of treatment, and methods of manufacturing a medicament for treatment involving a composition which is described as containing these components (i) and (ii). For convenience, this composition will be referred to in this specification as the "composition of the invention", although there are a number of combinations of components embodying the invention which are compositions according to the invention. Moreover, the components (i) and (ii) may be present in a concentration which either arrests, or does not arrest, a heart. These two classes of compositions are used in different ways in the invention described in the specification, and are referred to respectively as an "arresting" concentration of the composition and a "non-arresting" concentration of the composition contacting the cell, tissue or organ. In one form, the arresting composition contains adenosine and lignocaine, each at greater than 0.1 mM (and preferably below 20 mM). In one form of the non-arresting composition, adenosine and lignocaine are both below 0.1 mM and preferably 50 nM to 95 uM, or more preferably from 1 uM to 90 uM, measured as the concentration contacting the cells (ie, initially higher concentrations may be diluted with other components before contacting cells). It will be appreciated that the concentrations may be diluted by body fluids or other fluids that may be administered with the composition. For example, containers (such as vials) may be diluted 1 to 100 parts of blood, plasma, crystalloid or blood substitute prior to administration. Suitable methods to determine the arresting and non-arresting concentrations are described in WO00/56145 (U.S. Pat. No. 6,955,814) together techniques for assessing effectiveness.

In a further form, the invention provides use of (i) a potassium channel opener or agonist and/or an adenosine receptor agonist; and (ii) an antiarrhythmic agent, for the preparation of a medicament for reducing injury to cells, tissues or organs of a body. Preferably the cells, tissues or organs are ex vivo and/or recently implanted and/or being prepared for explantation. The use preferably includes administering the medicament in one or more of the ways set out elsewhere in this specification.

The term "tissue" is used herein in its broadest sense and refers to any part of the body exercising a specific function including organs and cells (native, donor, grown or cloned) or parts thereof, for example, cell clones, stem cells, cell lines or organelle preparations. Other examples include circulatory organs such as the heart, blood vessels and vasculature, respiratory organs such as the lungs, urinary organs such as the kidneys or bladder, digestive organs such as the stomach, liver, pancreas or spleen, reproductive organs such as the scrotum, testis, ovaries or uterus, neurological organs such as the brain, germ cells such as spermatozoa or ovum and somatic cells such as skin cells, cloned cells, stem cells, heart cells ie, myocytes, nerve cells, brain cells or kidney cells. The tissues may come from human or animal donors. The donor organs may also be suitable for xenotransplantation.

The term "organ" is used herein in its broadest sense and refers to any part of the body exercising a specific function including tissues and cells (native, donor, grown or cloned) or parts thereof, for example, endothelium, epithelium, blood brain barrier, cell lines or organelle preparations. Other examples include circulatory organs such as the blood vessels, heart, respiratory organs such as the lungs, urinary organs such as the kidneys or bladder, digestive organs such as the stomach, liver, pancreas or spleen, reproductive organs such as the scrotum, testis, ovaries or uterus, neurological organs such as the brain, germ cells such as spermatozoa or ovum and somatic cells such as skin cells, cloned cells, stem cells, heart cells i.e., myocytes, nerve cells, brain cells or kidney cells.

It will also be understood that the term "comprises" (or its grammatical variants) as used in this specification is equivalent to the term "includes" and should not be taken as excluding the presence of other elements or features.

Potassium channel openers are agents which act on potassium channels to open them through a gating mechanism. This results in efflux of potassium across the membrane along its electrochemical gradient which is usually from inside to outside of: the cell. Thus potassium channels are targets for the actions of transmitters, hormones, or drugs that modulate cellular function. It will be appreciated that the potassium: channel openers include the potassium channel agonists which also stimulate the activity of the potassium channel with the same result. It will also be appreciated that there are diverse classes of compounds which open or modulate different potassium channels; for example, some channels are voltage dependent, some rectifier potassium channels are sensitive to ATP depletion, adenosine and opioids, others are activated by fatty acids, and other channels are modulated by ions such as sodium and calcium (ie. channels which respond to changes in cellular sodium and calcium). More recently, two pore potassium channels have been discovered and thought to function as background channels involved in the modulation of the resting membrane potential.

Potassium channel openers may be selected from the group consisting of: nicorandil, diazoxide, minoxidil, pinacidil, aprikalim, cromokulim and derivative U-89232, P-1075 (a selective plasma membrane KATP channel opener), emakalim, YM-934, (+)-7,8-dihydro-6,6-dimethyl-7-hydroxy-8-(2-oxo-1-piperidinyl)-6H-pyrano[2,3-f]benz-2,1,3-oxadiazole (NIP-121), RO316930, RWJ29009, SDZ-PCO400, emakalim, symakalim, YM099, 2-(7,8-dihydro-6,6-dimethyl-6H-[1,4]oxazino[2,3-f][2,1,3]benzoxadiazol-8-yl) pyridine N-oxide, 9-(3-cyanophenyl)-3,4,6,7,9,10-hexahydro-1,8-(2H,5H)-acridinedione (ZM244085), [(9R)-9-(4-fluoro-3-125iodophenyl)-2,3,5,9-tetrahydro-4H-pyrano[3,4-b]thieno[2,3-e]pyridin-8(7H)-one-1,1-dioxide] ([125I]A-312110), (−)—N-(2-ethoxyphenyl)-N'-(1,2,3-trimethylpropyl)-2-nitroethene-1,1-diamine (Bay X 9228), N-(4-benzoyl phenyl)-3,3,3-trifluoro-2-hydroxy-2-methyl-propionamine (ZD6169), ZD6169 (KATP opener) and ZD0947 (KATP opener), WAY-133537 and a novel dihydropyridine potassium channel opener, A-278637. In addition, potassium channel openers can be selected from BK-activators (also called BK-openers or BK(Ca)-type potassium channel openers or large-conductance calcium-activated potassium channel openers) such as benzimidazolone derivatives NS004 (5-trifluoromethyl-1-(5-chloro-2-hydroxyphenyl)-1,3-dihydro-2H-benzimidazole-2-one), NS1619 (1,3-dihydro-1-[2-hydroxy-5-(trifluoromethyl)phenyl]-5-(trifluoromethyl)-2H-benzimidazol-2-one), NS1608 (N-(3-(trifluoromethyl)phenyl)-N'-(2-hydroxy-5-chlorophenyl) urea), BMS-204352, retigabine (also GABA agonist). There are also intermediate (eg. benzoxazoles, chlorzoxazone and zoxazolamine) and small-conductance calcium-activated potassium channel openers. Other compounds that are believed to open KATP channels include Levosimendan, glyceryl trinitrate (GTN), and hydrogen sulphide gas ($H_2S$) or the $H_2S$ donors (eg sodium hydrosulphide, NaHS).

In addition, potassium channel openers may act as indirect calcium antagonists ie they act to reduce calcium entry into the cell by shortening the cardiac action potential duration through the acceleration of phase 3 repolarisation, and thus shorten the plateau phase. Reduced calcium entry is thought to involve L-type calcium channels, but other calcium channels may also be involved.

Adenosine (6-amino-9-β-D-ribofuranosyl-9H-purine) is particularly preferred as the potassium channel opener. Adenosine is capable of opening the potassium channel, hyperpolarising the cell, depressing metabolic function, protecting endothelial cells, enhancing preconditioning of tissue and protecting from ischaemia or damage. Adenosine is also an indirect calcium antagonist, vasodilator, antiarrhythmic, antiadrenergic, free radical scavenger, arresting agent, anti-inflammatory agent (attenuates neutrophil activation), metabolic agent and possible nitric oxide donor. More recently, adenosine is known to inhibit several steps which can lead to slowing of the blood clotting process. In addition, elevated levels of adenosine in the brain has been shown to cause sleep and may be involved in different forms of dormancy. An adenosine analogue, 2-chloro-adenosine, may be used.

Suitable adenosine receptor agonists may be selected from: $N^6$-cyclopentyladenosine (CPA), N-ethylcarboxamido adenosine (NECA), 2-[p-(2-carboxyethyl)phenethyl-amino-5'-N-ethylcarboxamido adenosine (CGS-21680), 2-chloroadenosine, N⁶-[2-(3,5-demethoxyphenyl)-2-(2-methoxyphenyl]ethyladenosine, 2-chloro-N⁶-cyclopentyladenosine (CCPA), N-(4-aminobenzyl)-9-[5-(methylcarbonyl)-beta-D-robofuranosyl]-adenine (AB-MECA), ([IS-[1a,2b,3b,4a (S*)]]-4-[7-[[2-(3-chloro-2-thienyl)-1-methyl-propyl] amino]-3H-imidazole[4,5-b]pyridyl-3-yl]cyclopentane carboxamide (AMP579), N⁶-(R)-phenylisopropyladenosine (R-PLA), aminophenylethyladenosine (APNEA) and cyclohexyladenosine (CHA). Others include full adenosine A1 receptor agonists such as N-[3-(R)-tetrahydrofuranyl]-6-aminopurine riboside (CVT-510), or partial agonists such as CVT-2759 and allosteric enhancers such as PD81723. Other agonists may include N6-cyclopentyl-2-(3-phenylaminocarbonyltriazene-1-yl) adenosine (TCPA), a very selective agonist with high affinity for the human adenosine A1 receptor and allosteric enhancers of A1 adenosine receptor includes the 2-amino-3-napthoylthiophenes. Other adenosine enhancers could be selected to have similar effect.

Some embodiments of the invention utilize alpha-adrenergic receptor antagonists also known as alpha-adrenergic blocking agents, alpha-blocking agents, or, more commonly, alpha-blockers. Alpha-blockers include Methyldopa, Doxazosin, Clonidine, Phenoxybenzamine (a nonselective alpha1/alpha2-adrenergic receptor antagonist), Guanadrel, Terazosin, Prazosin, Guanfacine, Guanabenz, Phentolamine and Reserpine. Importantly alpha-adrenergic antagonists can also act as possible calcium channel inhibitors. Adenosine, as mentioned above is also an antiadrenergic.

Some embodiments of the invention utilize myosin light chain kinase inhibitors which can assist in relaxing smooth muscle. The myosin light chain kinase inhibitor may be a microbial product wortmannin, ML-7 (1-(5-iodonaphthalene-1-sulfonyl)-1H-hexahydro-1,4-diazepine.HCl), ML-9, myosin Light Chain Kinase Inhibitor Peptide 18), calmodulin antagonists (e.g W-7 and trifluoperazine), Rho kinase inhibitors (eg HA1077 or fausdil) and botulotoxin (discussed elsewhere).

Some embodiments of the invention utilize phosphodiesterase inhibitors (eg. papaverine, milrinone, theophylline, dipyridamole (discussed elsewhere)

Some embodiments of the invention include nitric oxide donors. Preferably, the NO donor is either 1) nitric-oxide synthase independent (such as nitroprusside, nitroglycerine or glycerine trinitrate (GTN), flurbiprofen or its NO-donating derivative, HCT1026 (2-fluoro-a-methyl[1,1'-biphenyl]-4-acetic acid and 4-(nitrooxy)butyl ester) or 2) nitric-oxide synthase dependent (such as L-arginine). In general all classes of nitric oxide donors range from organic nitrates to nitroso compounds, guanidines and metal-NO complexes. Thus NO donors can be those compounds, that release NO or one of its redox congeners spontaneously and those that require enzymatic metabolism to generate NO. Other examples of NO donors include diazeniumdiolate, pentaerythritol tetranitrate, polyalkyleneamine, tertiary and quaternary amino aliphatic NO donor compounds, Also NO donors would include NO-related redox signalling compounds to protect against oxidative stress.

Some embodiments of the invention utilize direct calcium antagonists, the principal action of which is to reduce calcium entry into the cell. These are selected from at least five major classes of calcium channel blockers as explained in more detail below. It will be appreciated that these calcium antagonists share some effects with potassium channel openers, particularly ATP-sensitive potassium channel openers, by inhibiting calcium entry into the cell.

Calcium channel blockers are also called calcium antagonists or calcium blockers. They are often used clinically to decrease heart rate and contractility and relax blood vessels. They may be used to treat high blood pressure, angina or discomfort caused by ischaemia and some arrhythmias, and they share many effects with beta-blockers, which could also be used to reduce calcium. Beta-blockers (or beta-adrenergic blocking agents) include atenolol (Tenormin™), propranolol hydrochloride (such as Inderal™), esmolol hydrochloride (Brevibloc™), metoprolol succinate (such as Lopressor™ or Toprol XL™), acebutolol hydrochloride (Sectral™), carteolol (such as Cartrol™), penbutolol sulfate (Levatol™) and pindolol (Visken™).

Five major classes of calcium channel blockers are known with diverse chemical structures: 1. Benzothiazepines: eg Diltiazem, 2. Dihydropyridines: eg nifedipine, Nicardipine, nimodipine and many others, 3. Phenylalkylamines: eg Verapamil, 4. Diarylaminopropylamine ethers: eg Bepridil, 5. Benzimidazole-substituted tetralines: eg Mibefradil.

The traditional calcium channel blockers bind to L-type calcium channels ("slow channels") which are abundant in cardiac and smooth muscle which helps explain why these drugs have selective effects on the cardiovascular system. Different classes of L-type calcium channel blockers bind to different sites on the alpha1-subunit, the major channel-forming subunit (alpha2, beta, gamma, delta subunits are also present). Different sub-classes of L-type channel are present which may contribute to tissue selectivity. More recently, novel calcium channel blockers with different specificities have also been developed for example, Bepridil, is a drug with Na+ and K+ channel blocking activities in addition to L-type calcium channel blocking activities. Another example is Mibefradil, which has T-type calcium channel blocking activity as well as L-type calcium channel blocking activity.

Three common calcium channel blockers are diltiazem (Cardizem), verapamil (Calan) and Nifedipine (Procardia). Nifedipine and related dihydropyridines do not have significant direct effects on the atrioventricular conduction system or sinoatrial node at normal doses, and therefore do not have direct effects on conduction or automaticity. While other calcium channel blockers do have negative chronotropic/dromotropic effects (pacemaker activity/conduction velocity). For example, Verapamil (and to a lesser extent diltiazem) decreases the rate of recovery of the slow channel in AV conduction system and SA node, and therefore act directly to depress SA node pacemaker activity and slow conduction. These two drugs are frequency- and voltage-dependent, making them more effective in cells that are rapidly depolarizing. Verapamil is also contraindicated in combination with beta-blockers due to the possibility of AV block or severe depression of ventricular function. In addition, mibefradil has negative chronotropic and dromotropic effects. Calcium channel blockers (especially verapamil) may also be particularly effective in treating unstable angina if underlying mechanism involves vasospasm.

Omega conotoxin MVIIA (SNX-111) is an N type calcium channel blocker and is reported to be 100-1000 fold more potent than morphine as an analgesic but is not addictive. This conotoxin is being investigated to treat intractable pain. SNX-482 a further toxin from the venom of a carnivorous spider venom, blocks R-type calcium channels. The compound is isolated from the venom of the African tarantula, Hysterocrates gigas, and is the first R-type calcium channel blocker described. The R-type calcium channel is believed to play a role in the body's natural communication network where it contributes to the regulation of brain function. Other Calcium channel blockers from animal kingdom include Kurtoxin from South African Scorpion, SNX-482 from African Tarantula, Taicatoxin from the Australian Taipan snake, Agatoxin from the Funnel Web Spider, Atracotoxin from the Blue Mountains Funnel Web Spider, Conotoxin from the Marine Snail, HWTX-I from the Chinese bird spider, Grammotoxin SIA from the South American Rose Tarantula. This list also includes derivatives of these toxins that have a calcium antagonistic effect.

Direct ATP-sensitive potassium channel openers (eg nicorandil, aprikalem) or indirect ATP-sensitive potassium channel openers (eg adenosine, opioids, levosimendan, glyceryl trinitrate) are also indirect calcium antagonists and reduce calcium entry into the tissue. One mechanism believed for ATP-sensitive potassium channel openers also acting as calcium antagonists is shortening of the cardiac action potential duration by accelerating phase 3 repolarisation and thus shortening the plateau phase. During the plateau phase the net influx of calcium may be balanced by the efflux of potassium through potassium channels. The enhanced phase 3 repolarisation may inhibit calcium entry into the cell by blocking or inhibiting L-type calcium channels and prevent calcium (and sodium) overload in the tissue cell.

Calcium channel blockers can be selected from nifedipine, nicardipine, nimopidipine, nisoldipine, lercanidipine, telodipine, angizem, altiazem, bepridil, amlopidine, felodipine, isradipine and cavero and other racemic variations.

In a preferred form, the potassium channel opener or agonist and/or an adenosine receptor agonist has a blood half-life of less than one minute, preferably less than 20 seconds.

In some embodiments, the composition may include additional potassium channel openers or agonists, for example diazoxide or nicorandil.

The inventor has also found that the inclusion of diazoxide with a potassium channel opener or adenosine receptor agonist and a local anaesthetic reduces injury. Thus in another aspect, the composition according to the invention further includes diazoxide.

Diazoxide is a potassium channel opener and in the present invention it is believed to preserve ion and volume regulation, oxidative phosphorylation and mitochondrial membrane integrity (appears concentration dependent). More recently, diazoxide has been shown to provide cardioprotection by reducing mitochondrial oxidant stress at reoxygenation. At present it is not known if the protective effects of potassium channel openers are associated with modulation of reactive oxygen species generation in mitochondria. Preferably the concentration of the diazoxide is between about 1 to 200 uM. Typically this is as an effective amount of diazoxide. More preferably, the concentration of diazoxide is about 10 uM.

The inventor has also found that the inclusion of nicorandil with a potassium channel opener or adenosine receptor agonist and a local anaesthetic reduces injury. Thus in another aspect, the composition according to the invention further includes nicorandil.

Nicorandil is a potassium channel opener and nitric oxide donor which can protect tissues and the microvascular integrity including endothelium from ischemia and reperfusion damage. Thus it can exert benefits through the dual action of opening KATP channels and a nitrate-like effect. Nicorandil can also reduce hypertension by causing blood vessels to dilate which allows the heart to work more easily by reducing both preload and afterload. It is also believed to have anti-inflammatory and anti-proliferative properties which can further attenuates ischemia/reperfusion injury.

The composition according to the invention also includes an antiarrhythmic agent. Antiarrhythmic agents are a group of pharmaceuticals that are used to suppress fast rhythms of the heart (cardiac arrhythmias). The following table indicates the classification of these agents.

| CLASS | Channel effects | Repolarisation Time | Drug Examples |
|---|---|---|---|
| IA | Sodium block | Prolongs | Quinidine, disopyramide, Procaine |
| IB | Sodium block | Shortens | Lidocaine, phenytoin, mexiletine, Tocainide |
| IC | Sodium block | Unchanged | Flecainide Propafenone, moricizine |
| II | Phase IV (depolarising current); Calcium channel | Unchanged | Beta-blockers including sotalol |
| III | Repolarising Potassium Currents | Markedly prolongs | Amiodarone, Sotalol, bretylium |
| IVA | AV nodal calcium block | Unchanged | Verapamil, diltiazem |
| IVB | Potassium channel openers | Unchanged | Adenosine, ATP |

It will also be appreciated that the antiarrhythmic agent may induce local anaesthesia (or otherwise be a local anaesthetic), for example, mexiletine, diphenylhydantoin, prilocalne, procaine, mepivocaine, quinidine, disopyramide and Class 1B antiarrhythmic agents.

Preferably, the antiarrhythmic agent is a class I or class III agent. Amiodarone is a preferred Class III antiarrhythmic agent. More preferably, the antiarrhythmic agent blocks sodium channels. More preferably, the antiarrhythmic agent is a class IB antiarrhythmic agent. Class 1B antiarrhythmic agents include lignocaine or derivatives thereof, for example, QX-314.

Preferably the class 1B antiarrhythmic agent is Lignocaine. In this specification, the terms "lidocaine" and "lignocaine" are used interchangeably. Lignocaine is also known to be capable of acting as a local anaesthetic probably by blocking sodium fast channels, depressing metabolic function, lowering free cytosolic calcium, protecting against enzyme release from cells, possibly protecting endothelial cells and protecting against myofilament damage. At lower therapeutic concentrations lignocaine normally has little effect on atrial tissue, and therefore is ineffective in treating atrial fibrillation, atrial flutter, and supraventricular tachycardias. Lignocaine is also a free radical scavenger, an antiarrhythmic and has anti-inflammatory and anti-hypercoagulable properties. It must also be appreciated that at non-anaesthetic therapeutic concentrations, local anaesthetics like lignocaine would not completely block the voltage-dependent sodium fast channels, but would down-regulate channel activity and reduce sodium entry. As anti-arrhythmic, lignocaine is believed to target small sodium currents that normally continue through phase 2 of the action potential and consequently shortens the action potential and the refractory period.

As lignocaine can act by blocking sodium fast channels, it will be appreciated that other sodium channel blockers may be used instead of or in combination with the local anaesthetic in the method and composition of the present invention. It will also be appreciated that sodium channel blockers include compounds that act to substantially block sodium channels or at least downregulate sodium channels. Examples of suitable sodium channel blockers include venoms such as tetrodotoxin and the drugs primaquine, QX, HNS-32 (CAS Registry #186086-10-2), NS-7, kappa-opioid receptor agonist U50 488, crobenetine, pilsicamide, phenyloin, tocamide, mexiletine, NW-1029 (a benzylamino propanamide derivative), RS100642, riluzole, carbamazepine, flecamide, propafenone, amiodarone, sotalol, imipramine and moricizine, or any of derivatives thereof. Other suitable sodium channel blockers include: Vinpocetine (ethyl apovincaminate); and Beta-carboline derivative, nootropic beta-carboline (ambocarb, AMB). In one aspect, the composition according to the invention consists essentially of (i) a potassium channel opener or agonist and/or an adenosine receptor agonist; and (ii) a local anaesthetic.

In another aspect, the composition according to the invention may further include an opioid. The further addition of an opioid may have similar if not improved effect on the reduction of injury.

Opioids, also known or referred to as opioid agonists, are a group of drugs that inhibit opium (Gr opion, poppy juice) or morphine-like properties and are generally used clinically as moderate to strong analgesics, in particular, to manage pain, both peri- and post-operatively. Other pharmacological effects of opioids include drowsiness, respiratory depression, changes in mood and mental clouding without loss of consciousness.

Opioids are also believed to be involved as part of the 'trigger' in the process of hibernation, a form of dormancy characterised by a fall in normal metabolic rate and normal core body temperature. In this hibernating state, tissues are better preserved against damage that may otherwise be caused by diminished oxygen or metabolic fuel supply, and also protected from ischemia reperfusion injury.

There are three types of opioid peptides: enkephalin, endorphin and dynorphin. Opioids act as agonists, interacting with stereospecific and saturable binding sites, in the heart, brain and other tissues. Three main opioid receptors have been identified and cloned, namely mu, kappa, and delta receptors. All three receptors have consequently been classed in the G-protein coupled receptors family (which class includes adenosine and bradykinin receptors). Opioid receptors are further subtyped, for example, the delta receptor has two subtypes, delta-1 and delta-2.

Cardiovascular effects of opioids are directed within the intact body both centrally (ie, at the cardiovascular and respiratory centres of the hypothalamus and brainstem) and peripherally (ie, heart myocytes and both direct and indirect effects on the vasculature). For example, opioids have been shown to be involved in vasodilation. Some of the action of opioids on the heart and cardiovascular system may involve direct opioid receptor mediated actions or indirect, dose dependent non-opioid receptor mediated actions, such as ion channel blockade which has been observed with antiarrhythmic actions of opioids, such as arylacetamide drugs. It is also known that the heart is capable of synthesising or producing the three types of opioid peptides, namely, enkephalin, endorphin and dynorphin. However, only the delta and kappa opioid receptors have been identified on ventricular myocytes.

Without being bound by any mode of action, opioids are considered to provide cardioprotective effects, by limiting ischemic damage and reducing the incidence of arrhythmias, which are produced to counter-act high levels of damaging agents or compounds naturally released during ischemia. This may be mediated via the activation of ATP sensitive potassium channels in the sarcolemma and in the mitochondrial membrane and involved in the opening potassium channels. Further, it is also believed that the cardioprotective effects of opioids are mediated via the activation of ATP sensitive potassium channels in the sarcolemma and in the mitochondrial membrane. Thus it is believed that the opioid can be used instead or in combination with the potassium channel opener or adenosine receptor agonist as they are also involved in indirectly opening potassium channels.

It will be appreciated that the opioids include compounds (natural or synthetic) which act both directly and indirectly on opioid receptors. Opioids also include indirect dose dependent, non-opioid receptor mediated actions such as ion channel blockade which have been observed with the antiarrhythmic actions of opioids.

Accordingly, the opioid may be selected from enkephalins, endorphins and dynorphins. Preferably the opioid is an enkephalin which targets delta, kappa and/or mu receptors. More preferably the opioid is a delta opioid receptor agonist. Even more preferably the opioid is selected from delta-1-opioid receptor agonists and delta-2-opioid receptor agonists. [D-Pen 2, 5] enkephalin (DPDPE), is a particularly preferred delta-1-opioid receptor agonist.

The inclusion of a compound for minimizing or reducing the uptake of water by a cell in a tissue with a potassium channel opener or adenosine receptor agonist and a local anaesthetic assists in reducing injury to a body, such as a composition comprising sucrose, adenosine and lignocaine. Sucrose reduces water shifts as an impermeant. Impermeant agents such as sucrose, lactobionate and raffinose are too large to enter the cells and hence remain in the extracellular spaces within the tissue and resulting osmotic forces prevent cell swelling that would otherwise damage the tissue, which would occur particularly during storage of the tissue.

Thus in a further aspect, the composition according to the invention may further include at least one compound for minimizing or reducing the uptake of water by a cell in the cell, tissue or organ. Accordingly, these compounds are involved in the control or regulation of osmosis. One consequence is that a compound for minimizing or reducing the uptake of water by a cell in the tissue reduces cell swelling that is associated with oedema, such as oedema that can occur during ischemic injury.

Compounds for minimizing or reducing the uptake of water by a cell in a tissue are typically impermeants or receptor antagonists or agonists. An impermeant according to the present invention may be selected from one or more of the group consisting of: sucrose, pentastarch, hydroxyethyl starch, raffinose, trehalose, mannitol, gluconate, lactobionate, and colloids. Colloids include albumin, hetastarch, polyethylene glycol (PEG), Dextran 40, Dextran 60, Dextran 30 or other sizes of dextrans. Other compounds that could be selected for osmotic purposes include those from the major classes of osmolytes found in the animal kingdom including polyhydric alcohols (polyols) and sugars, other amino acids and amino-acid derivatives, and methylated ammonium and sulfonium compounds. Thus volume expanders may be colloid-based or crystalloid-based.

Preferably, the concentration of the compound for minimizing or reducing the uptake of water by the cells in the tissue is between about 5 to 500 mM. Typically this is an effective amount for reducing the uptake of water by the cells in the tissue. More preferably, the concentration of the compound for reducing the uptake of water by the cells in the tissue is between about 20 and 100 mM. Even more preferably the concentration of the compound for reducing the uptake of water by the cells in the tissue is about 70 mM.

In a further embodiment, the composition according to the invention may include more than one compound for minimizing or reducing the uptake of water by the cells in the tissue. For example, a combination of impermeants (raffinose, sucrose and pentastarch) may be included in the composition or even a combination of colloids, and fuel substrates may be included in the composition.

The composition according to the invention may be hypo, iso or hyper osmotic.

Cell swelling can also result from an inflammatory response which may be important during organ retrieval, preservation and surgical grafting. Substance P, an important pro-inflammatory neuropeptide is known to lead to cell oedema and therefore antagonists of substance P may reduce cell swelling. Indeed antagonists of substance P, (-specific neurokinin-1) receptor (NK-1) have been shown to reduce inflammatory liver damage, i.e., oedema formation, neutrophil infiltration, hepatocyte apoptosis, and necrosis. Two such NK-1 antagonists include CP-96,345 or [(2S,3S)-cis-2-(diphenylmethyl)-N-((2-methoxyphenyl)-methyl)-1-azabi-cyclo(2.2.2.)-octan-3-amine (CP-96,345)] and L-733,060 or [(2S,3S)$_3$-([3,5-bis(trifluoromethyl)phenyl]methoxy)-2-phenylpiperidine]. R116301 or [(2R-trans)-4-[1-[3,5-bis(trifluoromethyl)benzoyl]-2-(phenylmethyl)-4-piperidinyl]-N-(2,6-dimethylphenyl)-1-acetamide (S)-Hydroxybutanedioate] is another specific, active neurokinin-1 (NK(1)) receptor antagonist with subnanomolar affinity for the human NK(1) receptor (K(i): 0.45 nM) and over 200-fold selectivity toward NK(2) and NK(3) receptors. Antagonists of neurokinin receptors 2 (NK-2) that may also reduce cell swelling include SR48968 and NK-3 include SR142801 and SB-222200. Blockade of mitochondrial permeability transition and reducing the membrane potential of the inner mitochondrial membrane potential using cyclosporin A has also been shown to decrease ischemia-induced cell swelling in isolated brain slices. In addition glutamate-receptor antagonists (AP5/CNQX) and reactive oxygen species scavengers (ascorbate, Trolox(R), dimethylthiourea, tempol(R)) also showed reduction of cell swelling. Thus, the compound for minimizing or reducing the uptake of water by a cell in a tissue can also be selected from any one of these compounds.

It will also be appreciated that the following energy substrates can also act as impermeants. Suitable energy substrate can be selected from one or more from the group consisting of: glucose and other sugars, pyruvate, lactate, glutamate, glutamine, aspartate, arginine, ectoine, taurine, N-acetyl-beta-lysine, alanine, proline, beta-hydroxy butyrate and other amino acids and amino acid derivatives, trehalose, floridoside, glycerol and other polyhydric alcohols (polyols), sorbitol, myo-innositol, pinitol, insulin, alpha-keto glutarate, malate, succinate, triglycerides and derivatives, fatty acids and carnitine and derivatives. In one embodiment, the at least one compound for minimizing or reducing the uptake of water by the cells in the tissue is an energy substrate. The energy substrate helps with recovering metabolism. The energy substrate can be selected from one or more from the group consisting of glucose and other sugars, pyruvate, lactate, glutamate, glutamine, aspartate, arginine, ectoine, taurine, N-acetyl-beta-lysine, alanine, proline and other amino acids and amino acid derivatives, trehalose, floridoside, glycerol and other polyhydric alcohols (polyols), sorbitol, myo-innositol, pinitol, insulin, alpha-keto glutarate, malate, succinate, triglycerides and derivatives, fatty acids and carnitine and derivatives. Given that energy substrates are sources of reducing equivalents for energy transformations and the production of ATP in a cell, tissue or organ of the body, it will be appreciated that a direct supply of the energy reducing equivalents could be used as substrates for energy production. For example, a supply of either one or more or different ratios of reduced and oxidized forms of nicotinamide adenine dinucleotide (e.g. NAD or NADP and NADH or NADPH) or flavin adenine dinucleotides (FADH or FAD) could be directly used to supply bond energy for sustaining ATP production in times of stress. Preferably, beta-hydroxy butyrate is added to the composition of the invention for protecting, or reducing injury to, cells, a tissue or organ.

In addition to providing energy substrates to the whole body, organ, tissue or cell, improvements in metabolising these substrates may occur in the presence of hydrogen sulphide ($H_2S$) or $H_2S$ donors (eg NaHS). The presence of hydrogen sulphide ($H_2S$) or $H_2S$ donors (eg NaHS) may help metabolise these energy substrates by lowering energy demand during arrest, protect and preserve the whole body, organ, tissue or cell during periods of metabolic imbalance such ischemia, reperfusion and surgery. Concentrations of Hydrogen sulfide above 1 microM ($10^{-6}$ M) concentration can be a metabolic poison that inhibits respiration at Respiratory Complex IV, which is part of the mitochondria, respiratory chain that couples metabolising the high energy reducing equivalents from energy substrates to energy (ATP) generation and oxygen consumption. However, it has been observed at lower concentrations, below $10^{-6}$ M (eg $10^{-10}$ to $10^{-9}$M), hydrogen sulfide may reduce the energy demand of the whole body, organ, tissue or cell which may result in arrest, protection and preservation. In other words, very low levels of sulfide down-regulate mitochondria, reduce $O_2$ consumption and actually increase "Respiratory Control" whereby mitochondria consume less $O_2$ without collapsing the electrochemical gradient across the inner mitochondria membrane. Thus there are observations that a small amount of sulfide, either directly or indirectly, may close proton leak channels and better couple mitochondrial respiration to ATP production more tightly, and this effect may improve the metabolism of high energy reducing equivalents from energy substrates. There is also the possibility that a sulphur cycle exists between the cell cytosol and mitochondria in mammals, including humans, providing the sulphur concentration is low. The presence of a vestige sulphur cycle would be consistent with current ideas on the evolutionary origin of mitochondria and their appearance in eukaryote cells from a symbiosis between a sulfide-producing host cell and a sulfide-oxidizing bacterial symbiont. Thus, hydrogen sulphide ($H_2S$) or $H_2S$ donors (eg. NaHS) may be energy substrates themselves in addition to improving the metabolism of other energy substrates. Accordingly, in one form, the invention provides a composition as described above further including hydrogen sulphide or a hydrogen sulfide donor.

The inventor has also found that the inclusion of a compound for inhibiting transport of sodium and hydrogen ions across a plasma membrane of a cell in the tissue with a potassium channel opener or adenosine receptor agonist and a local anaesthetic assists in reducing injury.

Thus in another aspect, the composition according to the invention further includes a compound for inhibiting transport of sodium and hydrogen ions across a plasma membrane of a cell in the tissue.

The compound for inhibiting transport of sodium and hydrogen across the membrane of the cell in the tissue is also referred to as a sodium hydrogen exchange inhibitor. The sodium hydrogen exchange inhibitor reduces sodium and calcium entering the cell.

Preferably the compound for inhibiting transport of sodium and hydrogen across the membrane of the cell in the tissue may be selected from one or more of the group consisting of Amiloride, EIPA(5-(N-entyl-N-isopropyl)-amiloride), cariporide (HOE-642), eniporide, Triamterene (2,4,7-triamino-6-phenylteride), EMD 84021, EMD 94309, EMD 96785, EMD 85131, HOE 694. B11 B-513 and T-162559 are other inhibitors of the isoform 1 of the $Na^+/H^+$ exchanger.

Preferably, the sodium hydrogen exchange inhibitor is Amiloride (N-amidino-3,5-diamino-6-chloropyrzine-2-carboximide hydrochloride dihydrate). Amiloride inhibits the sodium proton exchanger ($Na^+/H^+$ exchanger also often abbreviated NHE-1) and reduces calcium entering the cell. During ischemia excess cell protons (or hydrogen ions) are believed to be exchanged for sodium via the $Na^+/H^+$ exchanger.

Preferably, the concentration of the compound for inhibiting transport of sodium and hydrogen across the membrane of the cell in the tissue is between about 1.0 nM to 1.0 mM. More preferably, the concentration of the compound for inhibiting transport of sodium and hydrogen across the membrane of the cell in the tissue is about 20 uM.

The inventor has also found that the inclusion of antioxidant with a potassium channel opener or adenosine receptor agonist and a local anaesthetic. Thus in another aspect, the composition of the present invention may further include an antioxidant.

Antioxidants are commonly enzymes or other organic substances that are capable of counteracting the damaging effects of oxidation in the tissue. The antioxidant component of the composition according to the present invention may be selected from one or more of the group consisting of: allopurinol, carnosine, histidine, Coenzyme Q 10, n-acetyl-cysteine, superoxide dismutase (SOD), glutathione reductase (GR), glutathione peroxidase (GP) modulators and regulators, catalase and the other metalloenzymes, NADPH and AND(P)H oxidase inhibitors, glutathione, U-74006F, vitamin E, Trolox (soluble form of vitamin E), other tocopherols (gamma and alpha, beta, delta), tocotrienols, ascorbic acid, Vitamin C, Beta-Carotene (plant form of vitamin A), selenium, Gamma Linoleic Acid (GLA), alpha-lipoic acid, uric acid (urate), curcumin, bilirubin, proanthocyanidins, epigallocatechin gallate, Lutein, lycopene, bioflavonoids, polyphenols, trolox(R), dimethylthiourea, tempol(R), carotenoids, coenzyme Q, melatonin, flavonoids, polyphenols, aminoindoles, probucol and nitecapone, 21-aminosteroids or lazaroids, sulphydryl-containing compounds (thiazolidine, Ebselen, dithiolethiones), and N-acetylcysteine. Other antioxidants include the ACE inhibitors (captopril, enalapril, lisinopril) which are used for the treatment of arterial hypertension and cardiac failure on patients with myocardial infarction. ACE inhibitors exert their beneficial effects on the reoxygenated myocardium by scavenging reactive oxygen species. Other antioxidants that could also be used include beta-mercaptopropionylglycine, 0-phenanthroline, dithiocarbamate, selegilize and desferrioxamine (Desferal), an iron chelator, has been used in experimental infarction models, where it exerted some level of antioxidant protection. Spin trapping agents such as 5'-5-dimethyl-1-pyrrolione-N-oxide (DMPO) and (a-4-pyridyl-1-oxide)-N-t-butylnitrone (POBN) also act as antioxidants. Other antioxidants include: nitrone radical scavenger alpha-phenyl-tert-N-butyl nitrone (PBN) and derivatives PBN (including disulphur derivatives); N-2-mercaptopropionyl glycine (MPG) a specific scavenger of the OH free radical; lipooxygenase inhibitor nordihydroguaretic acid (NDGA); Alpha Lipoic Acid; Chondroitin Sulfate; L-Cysteine; oxypurinol and Zinc.

Preferably, the antioxidant is allopurinol (1H-Pyrazolo[3,4-a]pyrimidine-4-ol). Allopurinol is a competitive inhibitor of the reactive oxygen species generating enzyme xanthine oxidase. Allopurinol's antioxidative properties may help preserve myocardial and endothelial functions by reducing oxidative stress, mitochondrial damage, apoptosis and cell death. Preferably, the concentration of the antioxidant is between about 1 nM to 100 uM.

The inventor has also found that the inclusion of particular amounts of calcium and magnesium ions with a potassium channel opener or adenosine receptor agonist and a local anaesthetic reduces injury. The effect of the particular amounts of calcium and magnesium ions is to control the amount of ions within the intracellular environment. Calcium ions tend to be depleted, exported or otherwise removed from the intracellular environment and magnesium ions tend to be increased or otherwise restored to the levels typically found in a viable, functioning cell.

Thus in another aspect, the composition according to the invention further includes a source of magnesium in an amount for increasing the amount of magnesium in a cell in body tissue. Preferably the magnesium is present at a concentration of between 0.5 mM to 20 mM, more preferably about 2.5 mM.

In addition, typical buffers or carriers (which are discussed in more detail below) in which the composition of the invention is administered typically contain calcium at concentrations' of around 1 mM as the total absence of calcium has been found to be detrimental to the cell, tissue or organ. In one form, the invention also includes using carriers with low calcium (such as for example less than 0.5 mM) so as to decrease the amount of calcium within a cell in body tissue, which may otherwise build up during surgery or storage of cells, a tissue or organ. As described in the present invention, elevated magnesium and low calcium has been associated with protection during ischemia and reoxygenation of an organ. The action is believed to be due to decreased calcium loading. Preferably the calcium present is at a concentration of between 0.1 mM to 0.8 mM, more preferably about 0.3 mM.

In one embodiment, the composition includes elevated magnesium ions. Magnesium sulphate and magnesium chloride is a suitable source. In another embodiment, the composition includes a cellular transport enzyme inhibitor, such as dipyridamole, to prevent metabolism or breakdown of components in the composition.

In a further aspect, the invention provides a composition including an antiarrhythmic agent and one or more of:
  potassium channel opener,
  nitric oxide donor
  opioid;
  at least one compound for reducing uptake of water;
  sodium hydrogen exchange inhibitor,
  antioxidant; and
  a source of magnesium in an amount for increasing the amount of magnesium in a cell in body tissue.

The processes of inflammation and thrombosis are linked through common mechanisms. Therefore, it is believed that understanding of the processes of inflammation will help with better management of thrombotic disorders including the treatment of acute and chronic ischaemic syndromes. In the clinical and surgical settings, a rapid response and early intervention to an organ or tissue damaged from ischemia can involve both anti-inflammatory and anti-clotting therapies. In addition to protease inhibitors which attenuate the inflammatory response, further anti-inflammatory therapies have included the administration of aspirin, normal heparin, low-molecular-weight heparin (LMWH), non-steroidal anti-inflammatory agents, anti-platelet drugs and glycoprotein (GP) IIb/IIIa receptor inhibitors, statins, angiotensin converting enzyme (ACE) inhibitor, angiotensin blockers and antagonists of substance P. Examples of protease inhibitors are indinavir, nelfinavir, ritonavir, lopinavir, amprenavir or the broad-spectrum protease inhibitor aprotinin, a low-molecular-weight heparin (LMWH) is enoxaparin, non-steroidal anti-inflammatory agent are indomethacin, ibuprofen, rofecoxib, naproxen or fluoxetine, an anti-platelet drug is Clopidogrel or aspirin, a glycoprotein (GP) IIb/IIIa receptor inhibitor is abciximab, a statin is pravastatin, an angiotensin converting enzyme (ACE) inhibitor is captopril and an angiotensin blocker is valsartin.

Accordingly, in another embodiment of the invention, a selection of these agents is added to a composition according to the invention to deliver improved management of inflammation and clotting. Alternatively, the composition according to the invention may be administered together with any one or more of these agents.

In particular, protease inhibitors attenuate the systemic inflammatory response in patients undergoing cardiac surgery with cardiopulmonary bypass, and other patients where the inflammatory response has been heightened such as AIDS or in the treatment of chronic tendon injuries. Some broad spectrum protease inhibitors such as aprotinin are also reduce blood loss and need for blood transfusions in surgical operations such as coronary bypass.

Compounds that substantially prevent the breakdown of adenosine in the blood such as nucleoside transport inhibitors, such as dipyridamole could be are used as additives in the composition of the invention. The half life of adenosine in the blood is about 10 seconds so the presence of a medicament to substantially prevent its breakdown will maximise the effect of the composition of the present invention.

Dipyridamole is advantageously included in a concentration from about 0.01 microM to about 10 mM, preferably 0.05 to 100 microM, and has major advantages with respect to cardioprotection. Dipyridamole may supplement the actions of adenosine by inhibiting adenosine transport and breakdown leading to increased protection of cells, tissues and organs of the body during times of stress. Dipyridamole may also be administered separately for example by 400 mg daily tablets to produce a plasma level of about 0.4 microgram/ml, or 0.8 microM concentration. Other antiproliferative drugs which may optionally be included are paclitaxel (0-100 microg/mL), and tranilast (0-300 microg/mL).

In some embodiments, the composition may further include toxins. These may include the conotoxins referred to above (such as the N type calcium channel blockers) and toxins such as Botulinum toxin ("botox") which promote smooth muscle relaxation. Botulinum toxin type A is a neurotoxin protein complex produced by the bacteria (*clostridium botulinum*) that can cause food poisoning known as botulism. There are seven or more known types of *C. Botulinum* toxin, but only types A (BOTOX® Cosmetic) and B (Myobloc®) are used as medical treatments. The type A toxin affects the nerves and when injected in small amounts into a muscle, the muscle relaxes and reduces its metabolic activity. The toxin is injected at multiple sites to ensure complete dispersal of toxin through the target regions. Normally, multiple 0.1 ml therapeutic effective injections containing 5 to 20 U per injection site are used for treatments with a total dose per patient not normally exceeding about 100-150 U. At higher concentrations (above 20 U), the toxin has also been shown to directly inhibit smooth muscle contractility as evidenced by the decreased contractile response to ACh. Thus doses of the Botulinum toxin type A can be between about 0.01 U/kg and about 35 U/kg. Above 35 U/kg is approaching the toxic dose, and the lethal human dose is about 200-300 pg/kg. Botulinum toxin type A is currently used to treat dystonia. In one form of the invention, the composition further includes Botulinum toxin type A, preferably at 1 to 35 U/ml. Botulinum toxin type B (NeuroBloc) may alternatively be used.

In another aspect of the invention, antibiotics such as vancomycin, cefotaxime, and gentamicin are present in the graft solution to minimise transmission of infection, such as during surgical attachment and therefore loss of patency. Also, the composition of the invention may further include cryoprotective glycerol, trehalose, high glucose concentrations (above 200 mM) or other additives that inhibit the intracellular water from freezing and damaging or fracturing the cell membrane. This permits the grafts to be stored below freezing until use.

The composition according to the present invention is highly beneficial at about 10° C. but can also be used to prevent injury over a wider temperature range up to about 37° C. The composition according to the invention may be used at a temperature range selected from the following: 0° C. to 5° C., 5° C. to 20° C., 20° C. to 32° C. and 32° C. to 38° C.

The composition may be administered intravenously or be administered both intravenously and intraperitoneally or in special circumstances directly accessing a major artery such as the femoral artery or aorta, for example in patients who have no pulse. In one embodiment, the composition of the invention may be administered intravenously and intraperineally simultaneously, the perineum acting as, in effect, a reservoir of composition for the bloodstream as well as acting on organs in the vicinity with which it comes into contact.

As described herein, in particular embodiments of the invention, the composition of the present invention protects and preserves tissue of a body with good to excellent recoveries of function or viability of body tissue after reperfusion. Affecting viability of a tissue during preservation and recovery of the body tissue, such that affected tissue remains viable or living during those processes and is capable of returning to its function, particularly after the tissue has been subject to shock, is important to patient welfare.

Preferably, the invention reduces injury to affected tissue, such that the tissue is capable of returning to its function. Maintaining or stabilising the tissue in a viable state includes maintaining the membrane potential of tissue cells at or around resting level, so as to reduce sodium or calcium loading of the cell which is a cause of injury during ischaemia and reperfusion. Preservation is known as the act or process of preserving the tissue or keeping from injury, destruction or decay. In this application, the composition according to the invention acts to minimise any potential injury, destruction or decay of cells, a tissue or organ, particularly during surgery, especially surgery involving excision of tissue and its implantation or grafting.

The composition of the present invention is particularly useful in reducing injury to heart tissue during heart surgery (open-heart or robotic heart surgery), including heart transplants, and neonate/infant hearts. Other applications include reducing heart damage before, during or following cardiovascular intervention which may include a heart attack, angioplasty or angiography. For example, the composition may be administered to subjects who have suffered or are developing a heart attack and used at the time of administration of blood clot-busting drugs such as streptokinase. As the clot is dissolved, the presence of the composition may protect the heart from further injury such as reperfusion injury. The composition may be particularly effective as a cardioprotectant in those portions of the heart that have been starved of normal flow, nutrients and/or oxygen for different periods of time. For example, the pharmaceutical composition may also be used to treat heart ischaemia which could be pre-existing or induced by cardiovascular intervention.

Accordingly, in another embodiment of the invention, there is provided a method of preserving cells, a tissue or organ of the body, such as a blood vessel, comprising administering a composition as described above. The composition may be administered prior to medical intervention affecting the cells, tissue or organ as well as, or alternatively following, any such medical intervention. Indeed, the invention is desirably used before, during and after the procedure so that a fluid of common composition is used throughout to minimise stress on and/or injury to the explanted tissue. The composition used in this embodiment of the invention may have an arresting or a non-arresting concentration of active components in it. In one form, the method includes administering a non-arresting concentration of the composition and, in another form, it has an arresting concentration of the composition (preferably as a bolus) followed by a non-arresting concentration of the composition.

In another embodiment, the present invention may be administered with or contain blood or blood products or artificial blood or oxygen binding molecules or solutions to improve the body's oxygen transport ability and survival by helping to reduce hypoxic and ischemic damage from blood loss. The oxygen-containing molecules, compounds or solutions may be selected from natural or artificial products. For example, an artificial blood-based product is perfluorocarbon-based or other haemoglobin-based substitute. Some of the components may be added to mimic human blood's oxygen transport ability such Hemopure™, Gelenpol™, Oxygent™, and PolyHeme™. Hemopore is based on a chemically stabilized bovine hemoglobin. Gelenpol is a polymerized hemoglobin which comprises synthetic water-soluble polymers and modified heme proteins. Oxygent is a perflubron emulsion for use as an intravenous oxygen carrier to temporarily substitute for red blood cells during surgery. Polyheme is a human hemoglobin-based solution for the treatment of life-threatening blood loss.

It is believed that the oxygenation of the body from a variety of ways including but not limited to oxygen gas mixture, blood, blood products or artificial blood or oxygen binding solutions maintains mitochondrial oxidation and this helps preserve the myocyte and endothelium of the organ. Without being bound by any particular mode or theory, the inventor has found that gentle bubbling with 95% $O_2$/5% $CO_2$ helps maintains mitochondrial oxidation which helps preserve the myocyte and coronary vasculature.

In one preferred embodiment of this aspect of the present invention with respect to whole body or organs outside the body, the composition is aerated with a source of oxygen before and/or during use. The source of oxygen may be an oxygen gas mixture where oxygen is the predominant component. The oxygen may be mixed with, for example, $CO_2$. Preferably, the oxygen gas mixture is 95% $O_2$ and 5% $CO_2$.

In another aspect of the present invention there is provided a method for protecting cells, a tissue or organ, preferably a blood vessel for implantation, including:
  providing in a suitable container a composition according to the invention;
  providing one or more nutrient molecules selected from the group consisting of blood, blood products, artificial blood and a source of oxygen;
  optionally aerating the composition with the oxygen (for example, in the case of isolated organs) or combining the nutrient molecules with the composition, or both; and
  placing the tissue in contact with the combined composition under conditions sufficient to reduce injury.

Preferably the oxygen source is an oxygen gas mixture. Preferably oxygen is the predominant component. The oxygen may be mixed with, for example $CO_2$. More preferably, the oxygen gas mixture is 95% $O_2$ and 5% $CO_2$. Preferably the composition is aerated before and/or during contact with the tissue.

The composition according to this aspect of the invention may be in liquid form. Liquid preparations of the pharmaceutical composition may take the form of, for example, solutions, syrups, or suspensions, or may be presented as a dry product for constitution with water or other suitable vehicle. Such liquid preparations may be prepared by conventional means with pharmaceutically acceptable additives such as suspending agents, emulsifying agents, non-aqueous vehicles, preservatives and energy sources. In another form, the invention comprises a composition in tablet form and in another form, the invention comprises an aerosol which could be administered via oral, skin or nasal routes.

In another aspect of the invention, there is provided a method of protecting vasculature tissue from reperfusion injury, including inflammatory and blood clotting and coagulation effects often experienced during reperfusion following an ischaemic event. The method comprises administering a solution comprising a non-arresting form of the composition according to the present invention, optionally following a bolus of an arresting form.

The body may be a human or an animal such as a livestock animal (eg, sheep, cow or horse), laboratory test animal (eg, mouse, rabbit or guinea pig) or a companion animal (eg, dog or cat), particularly an animal of economic importance. Preferably, the body is human.

The method of the present invention involves contacting a tissue with the composition according to the invention, for a time and under conditions sufficient for the tissue to be preconditioned, arrested, protected and/or preserved. The composition may be infused or administered as a bolus intravenous, intracoronary or any other suitable delivery route as pre-treatment for protection during a cardiac intervention such as open heart surgery (on-pump and off-pump), angioplasty (balloon and with stents or other vessel devices) and with clot-busters (anti-clotting drug or agents).

The composition may be administered intravenously or be administered both intravenously and intraperitoneally or in special circumstances directly accessing a major artery such as the femoral artery or aorta or in the carotid artery or another artery during aortic dissection to protect the brain from hypoxia or ischemia. In one embodiment, the composition of the invention may be administered intravenously and intraperineally simultaneously, the perineum acting as, in effect, a reservoir of composition for the bloodstream as well as acting on organs in the vicinity with which it comes into contact. Moreover, where the composition contains two or more components, these may be administered separately but simultaneously. Substantially simultaneous delivery of the component to the target site is desirable. This may be achieved by pre-mixing the components for administration as one composition, but that is not essential. The invention is directed towards the simultaneous increase in local concentration (for example an organ such as the heart) of the components of a composition according to the invention (for example, where a first component is (i) a potassium channel opener or agonist and/or an adenosine receptor agonist; and (ii) a local anaesthetic). One preferred form of the composition is a combination of adenosine and lignocaine.

Accordingly, the tissue may be contacted by delivering the composition according to the invention intravenously to the tissue. This involves using blood as a vehicle for delivery to the tissue. In particular, the composition according to the invention may be used for blood cardioplegia. Alternatively, the composition may be administered directly as a bolus by a puncture (eg, by syringe) directly to the tissue or organ, particularly useful when blood flow to a tissue or organ is limiting. The composition for arresting, protecting and preserving a tissue may also be administered as an aerosol, powder, solution or paste via oral, skin or nasal routes.

Alternatively, the composition may be administered directly to the tissue, organ or cell or to exposed parts of the internal body to reduce injury. In particular, the composition according to the invention may be used for crystalloid cardioplegia.

The composition according to the invention may be delivered according to one of or a combination of the following delivery protocols: intermittent, continuous and one-shot.

Accordingly, in another aspect of the invention, there is provided a composition for arresting, protecting and preserving a cell, tissue or organ of a body upon administration of a single dose of the composition, the composition including a primary potassium channel opener or agonist and/or adenosine receptor agonist and a local anaesthetic. The invention also provides a method for arresting and protecting an tissue comprising administering as a single dose an effective amount of that composition.

In another aspect of the invention, there is provided a composition for arresting, protecting and preserving a tissue by intermittent administration of the composition, the composition including an effective amount of a primary potassium channel opener or agonist and/or adenosine receptor agonist and a local anaesthetic. A suitable administration schedule is a 2 minute induction dose every 20 minutes throughout the period. The actual time periods can be adjusted based on observations by one skilled in the art administering the composition, and the animal/human model selected. The invention also provides a method for intermittently administering a composition for arresting, protecting and preserving a tissue.

The composition can of course also be used in continuous infusion with both normal and injured tissues or organs, such as heart tissue. Continuous infusion also includes static storage of the tissue, whereby the tissue is stored in a composition according to the invention, for example the tissue may be placed in a suitable container and immersed in a solution according to the invention for transporting donor tissues from a donor to recipient.

The dose and time intervals for each delivery protocol may be designed accordingly. For example, a composition according to the invention may be delivered as a one-shot to the tissue to initially arrest of the tissue. A further composition according to the invention may then be administered continuously to maintain the tissue in an arrested state. Yet a further composition according to the invention may be administered continuously to reperfuse the tissue or recover normal function.

As mentioned previously, the composition according to the invention may be used or contact the tissue at a temperature range selected from one of the following: from about 0° C. to about 5° C., from about 5° C. to about 20° C., from about 20° C. to about 32° C. and from about 32° C. to about 38° C. It is understood that "profound hypothermia" is used to describe a tissue at a temperature from about 0° C. to about 5° C. "Moderate hypothermia" is used to describe a tissue at a temperature from about 5° C. to about 20° C. "Mild hypothermia" is used to describe a tissue at a temperature from about 20° C. to about 32° C. "Normothermia" is used to describe a tissue at a temperature from about 32° C. to about 38° C., though the normal body temperature is around 37 to 38° C.

While it is possible for each component of the composition to contact the tissue alone, it is preferable that the components of the pharmaceutical composition be provided together with one or more pharmaceutically acceptable carriers, diluents, adjuvants and/or excipients. Each carrier, diluent, adjuvant and/or excipient must be pharmaceutically acceptable such that they are compatible with the components of the pharmaceutical composition and not harmful to the subject. Preferably, the pharmaceutical composition is prepared with liquid carriers, diluents, adjuvants and/or excipients.

The composition according to the invention may be suitable for administration to the tissue in liquid form, for example, solutions, syrups or suspensions, or alternatively they may be administered as a dry product for constitution with water or other suitable vehicle before use. Such liquid preparations may be prepared by conventional means.

The composition according to the invention may be suitable for topical administration to the tissue. Such preparation may be prepared by conventional means in the form of a cream, ointment, jelly, solution or suspension.

The composition may also be formulated as depot preparations. Such long acting formulations may be administered by implantation (eg, subcutaneously or intramuscularly) or by intramuscular injection. Thus, for example, the composition according to the invention may be formulated with suitable polymeric or hydrophobic materials (eg, as an emulsion in an acceptable oil or ion exchange resins, or as sparingly soluble derivatives, for example, as a sparingly soluble salt.

Accordingly, this aspect of the invention also provides a method for reducing injury, which includes providing the composition together with a pharmaceutically acceptable carrier, diluent, adjuvant and/or excipient. A preferred pharmaceutically acceptable carrier is a buffer having a pH of about 6 to about 9, preferably about 7, more preferably about 7.4 and/or low concentrations of potassium. For example, the composition has a total potassium concentration of up to about 10 mM, more preferably about 2 to about 8 mM, most preferably about 4 to about 6 mM. Suitable buffers include Krebs-Henseleit which generally contains 10 mM glucose, 117 mM NaCl, 5.9 mM KCl, 25 mM NaHCO$_3$, 1.2 mM NaH$_2$PO$_4$, 1.12 mMCaCl$_2$ (free Ca$^{2+}$=1.07 mM) and 0.512 mM MgCl$_2$ (free Mg$^{2+}$=0.5 mM), Tyrodes solution which generally contains 10 mM glucose, 126 mM NaCl, 5.4 mM KCl, 1 mM CaCl$_2$, 1 mM MgCl$_2$, 0.33 mM NaH$_2$PO$_4$ and 10 mM HEPES (N-[2-hydroxyethyl]piperazine-N'-[2-ethane sulphonic acid], Fremes solution, Hartmanns solution which generally contains 129 NaCl, 5 mM KCl, 2 mM CaCl$_2$ and 29 mM lactate and Ringers-Lactate. Other naturally occurring buffering compounds that exist in muscle that could be also used in a suitable ionic environment are carnosine, histidine, anserine, ophidine and balenene, or their derivatives. One advantage of using low potassium is that it renders the present composition less injurious to the subject, in particular paediatric subjects such as neonates/infants. High potassium has been linked to an accumulation of calcium which may be associated with irregular heart beats during recovery, heart damage and cell swelling. Neonates/infants are even more susceptible than adults to high potassium damage during cardiac arrest. After surgery a neonate/infant's heart may not return to normal for many days, sometimes requiring intensive therapy or life support.

It is also advantageous to use carriers having low concentrations of magnesium, such as, for example up to about 2.5 mM, but it will be appreciated that high concentrations of magnesium, for example up to about 20 mM, may be used if desired without substantially affecting the activity of the composition.

In another embodiment of the present invention there is provided use of a composition according to the present invention for reducing injury.

In the figures:

FIG. 1. Graph showing the effect of increasing the concentrations of adenosine on the tension of intact and denuded rat aortic rings precontracted with norepinephrine. The A (Adenosine) concentrations comprised 10, 50, 100, 200, 300, 400 and 500 uM (final concentrations), shown in log concentrations on the X axis.

Figure 2:
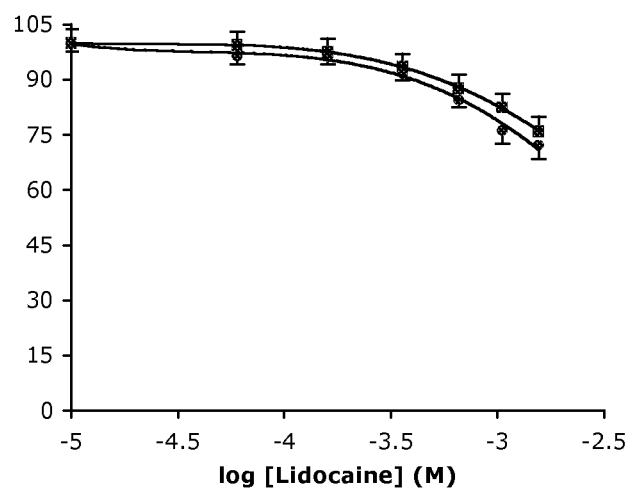

FIG. 2. Graph showing the effect of increasing the concentrations of lidocaine on the tension of intact and denuded rat aortic rings precontracted with norepinephrine. The L (Lidocaine) concentrations comprised 10, 50, 100, 200, 300, 400 and 500 uM (final concentrations), shown in log concentration on the X axis.

Figure 3:
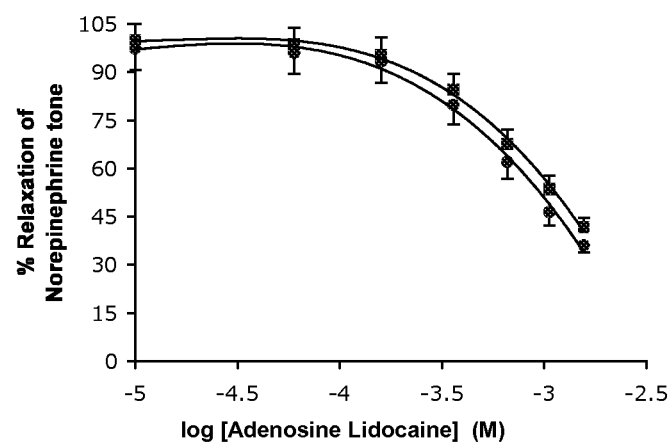

FIG. 3. Graph showing the effect of increasing the concentrations of adenosine and lidocaine (AL) on the tension of intact and denuded rat aortic rings precontracted with norepinephrine. The AL concentrations comprised 10 uM AL (10 uM A and 10 uM L), 10 uM AL (10 uM A and 10 uM L), 50 uM AL (50 uM A and 50 uM L), 100 uM AL (100 uM A and 100 uM L), 200 uM AL (200 uM A and 200 uM L), 300 uM AL (300 uM A and 300 uM L), 400 uM AL (400 uM A and 400 uM L), and 500 uM AL (50 uM A and 500 uM L), shown in log concentration on the X axis.

EXAMPLES

The following are provided as non-limiting examples of the invention for the purpose of illustrating the invention.

Example 1

Effect of Adenosine, Lidocaine and Adenosine Plus Lidocaine on Rat Aorta Muscle Tension and Relaxation This example illustrates the different effect on intact isolated vasculature rings of an adenosine-lidocaine solution according to the invention, which did not lead to relaxation by over 5% until 200 uM. Adenosine and AL (adenosine and lidocaine) show similar effects, and about 30% greater falls in relaxation than lidocaine alone at 400 and 500 uM concentrations when bathed in 10 mM glucose in Krebs-Henseleit at pH 7.4 37° C. under aerobic conditions (95% $O_2$ & 5% $CO_2$). A major difference between AL and adenosine alone is that the AL-induced relaxation profile is not dependent on an intact endothelium. The effect of AL in the denuded rings is as if the endothelium is not removed.

Animal Preparation: Male Sprague Dawley rats (300-350 g) were fed ad libitum and housed in a 12-hour light/dark cycle. On the day of the experiment rats were anaesthetized using $CO_2$ anaesthesia which has been shown to have less effect than pentobarbital to alter the vascular synthesis of prostacyclin and smooth muscle contractility which could interfere with the results (Butler M M et al Lab Anim Sci. 1990 40 277-83). Animals were treated in accordance with the Guide for the Care and Use of Laboratory Animals published by the US national Institutes of Health (NIH Publication No. 85-23, revised 1996). Lignocaine hydrochloride was sourced as a 2% solution (ilium) from the local Pharmaceutical Suppliers (Lyppard, Queensland). All other chemicals, including adenosine (A9251 >99% purity), were purchased from Sigma Aldrich (Castle Hill, NSW).

Aortic ring preparation and organ bath tension measurements: The abdominal and thoracic cavity of anaesthetised rats were opened and the thoracic aorta was removed and placed in a cold solution of Krebs Henseleit (117 mM NaCl, 5.9 mM KCl, 1.2 mM $Na_2PO_4$, 0.5 mM $MgCl_2$, 1.12 mM $CaCl_2$, 25 mM $NaHCO_3$) pH 7.4 with 10 mM glucose.

The aorta was carefully dissected from surrounding fat and connective tissue and cut into short transverse segments. Aortic rings (about 3 mm wide) were equilibrated in a standard 20 ml volume organ bath containing Krebs Henseleit (117 mM NaCl, 5.9 mM KCl, 1.2 mM $Na_2PO_4$, 0.5 mM $MgCl_2$, 1.12 mM $CaCl_2$, 25 mM $NaHCO_3$) pH 7.4 with 10 mM glucose and continuously bubbled with 95% $O_2$ and 5% $CO_2$ at 37° C. for 1 hour (zero tension). The rings were vertically mounted on small stainless steel stirrups and connected to an isometric force transducer coupled to a MacLab and computer. The ring tension was manually adjusted to 1.4 g and the rings allowed to equilibrate for 30 min. The aortic rings were then washed with freshly prepared Krebs Henseleit buffer pH 7.4 containing 10 mM glucose and the tension was readjusted to 1.4 g tension. Each preparation was contracted submaximally using 60 ul of 0.1 mM Noradrenalin (0.3 uM final concentration) (Zerkowski H R et al, 1993, Evans G R et al 1997) and those rings that failed to contract were discarded. After stabilisation, 20 ul of 10 mM acetylcholine (10 uM final concentration) was applied to confirm the presence or absence of an intact endothelium in all preparations. Acetylcholine will induce rapid relaxation of precontracted rings if the endothelium is intact, and will have little or no effect if the endothelium is damaged (or denuded) and the rings will remain in contracted state (Furchgott, R F et al Nature 1980, Nagao, T et al AJP 1992). Aortic rings were denuded by gently rubbing the intimal surface of the vessel segment with a smooth metal probe. After noradrenalin and acetylcholine additions, the rings were washed three times. The aortic rings were allowed to stabilize for 20 min and the tension adjusted to 1.4 g. Noradrenalin (0.3 uM) or in some cases depolarising potassium chloride (65 mM) was then added and the experiment commenced after stabilisation of tension (10-15 min). Adenosine, lidocaine or adenosine and lidocaine (AL) were added to the bath in a concentration-dependent manner and the change in tension of precontracted rings was assessed. Preliminary experiments showed that noradrenalin (0.3 uM) increased tension and plateaued after 10 min and remained at this level over the 60 min, the time course of each experiment. Adenosine alone and lidocaine alone concentration-response curves for intact and denuded aortic rings were obtained by adding 10, 50, 100, 200, 300, 400 and 500 uM (final concentrations). The AL concentration-response curves were obtained by adding 5 uM each of A+L (10 uM total), 25 uM each of A+L (50 uM total), 50 uM each of A+L (100 uM total), 100 uM each of A+L (200 uM total), 150 uM each of A+L (300 uM total), 200 uM each of A+L (400 uM total), 250 uM each of A+L (500 uM total).

Various compositions according to the invention as described above are illustrated as follows:

1 mM A and 1 mM L,
2 mM A and 2 mM L (compare to 0.5 mM each)
AL+NG-nitro-L-arginine methyl ester (L-NAME, 100 uM for 30 min) in denuded rings and intact rings. Involvement of NO is also assessed. At the plateau of the pre-contraction, A, L or AL are added in the bath and relaxation recorded.
AL+L-arginine (0.5 mM) precursor of endothelium-derived NO(NO donor) to confirm a role for eNOS (endothelial NO synthase) in adenosine endothelium-dependent relaxation.
AL+8-sulfophenyltheophyline (SPT) (non-specific Ado blocker) (100 uM)
AL+Pertussus Toxin
AL+glibenclamide (30 uM) (non-specific blocker of KATP channels
AL+mitoKATP channel blocker
AL+papaverine (0.5 mg/ml)
AL+GTN (0.5 mg/ml)
AL+16 mM $MgCl_2$ (can induce relaxation due to Ca entry inhibition)
AL+opioid agonist
AL+blood anti-coagulant (eg. heparin)
AL+naloxone (0.1 mM) (incubated for 20 min before adding AL)
AL+amilioride
AL+BoTox
AL+Ca activated K channel blocker (0.1 mM tetraethylammonium, TEA-Sigma Sahin A S et al 2005, also Langton P D et al AJP 260 H927-34, 1991))
AL+ultra-short-acting beta-blocker, esmolol
AL+60 mM KCL
AL+Ca activated channel blocker (0.1 mM tetraethylammonium, TEA-Sigma Sahin A S et al 2005)
AL+AMP579 (AMP579 is a mixed adenosine agonist with both A1 and A2 effects)
AL+5-hydroxydecanoate (5HD) (10 uM) specific blocker of mitochondrial $K_{ATP}$ channels Results:

Effect of increasing the concentration of adenosine, lidocaine and adenosine+lidocaine on the tension of intact and denuded are shown in FIGS. 1 to 3 respectively (n=6). Table 1 below shows tensions of intact and denuded isolated rat aortic rings using 0.3 uM norepinephrine followed by different concentrations of adenosine, lidocaine and adenosine-lidocaine (AL). Values are expressed grams (±S.E.M). Table 2 (below) shows extent of relaxation of intact and denuded isolated rat aortic rings using different concentrations of adenosine, lidocaine and adenosine-lidocaine (AL). Values are expressed as a percentage (±S.E.M) of precontracted norepinephrine (0.3 uM) tensions (see Table 1 for precontracted tensions).

TABLE 1

Tensions of intact and denuded isolated rat aortic rings using 0.3 uM norepinephrine followed by different concentrations of adenosine, lidocaine and adenosine-lidocaine (AL). Values are expressed grams (±S.E.M).

| Drugs | Type of aortic rings (n = 6) | Precontracted Tension (g) | Drug concentrations (μM) | | | | | | |
|---|---|---|---|---|---|---|---|---|---|
| | | | 10 | 60 | 160 | 360 | 660 | 1060 | 1560 |
| Adenosine | Intact | 3.68 ± 0.11 | 3.65 ± 0.12 | 3.54 ± 0.11 | 3.30 ± 0.09 | 2.81 ± 0.11 | 2.23 ± 0.14 | 1.78 ± 0.13 | 1.43 ± 0.08 |
| | Denuded | 3.55 ± 0.08 | 3.56 ± 0.08 | 3.55 ± 0.09 | 3.51 ± 0.09 | 3.39 ± 0.11 | 3.12 ± 0.14 | 2.73 ± 0.17 | 2.23 ± 0.17 |
| Lidocaine | Intact | 3.58 ± 0.07 | 3.57 ± 0.08 | 3.50 ± 0.08 | 3.44 ± 0.07 | 3.28 ± 0.07 | 3.02 ± 0.07 | 2.73 ± 0.13 | 2.59 ± 0.14 |
| | Denuded | 3.33 ± 0.13 | 3.32 ± 0.12 | 3.31 ± 0.12 | 3.24 ± 0.12 | 3.11 ± 0.12 | 2.92 ± 0.12 | 2.75 ± 0.12 | 2.53 ± 0.13 |
| AL | Intact | 3.78 ± 0.24 | 3.68 ± 0.25 | 3.63 ± 0.24 | 3.53 ± 0.25 | 3.02 ± 0.23 | 2.35 ± 0.21 | 1.76 ± 0.16 | 1.36 ± 0.09 |
| | Denuded | 3.71 ± 0.19 | 3.70 ± 0.19 | 3.66 ± 0.19 | 3.53 ± 0.21 | 3.13 ± 0.19 | 2.51 ± 0.17 | 1.99 ± 0.15 | 1.55 ± 0.11 |

TABLE 2

Extent of relaxation of intact and denuded isolated rat aortic rings using different concentrations of adenosine, lidocaine and adenosine-lidocaine (AL). Values are expressed as a percentage (±S.E.M) of precontracted norepinephrine (0.3 uM) tensions (see Table 1 for precontracted tensions).

| Drugs | Type of rings | Drug concentrations (μM) | | | | | | |
|---|---|---|---|---|---|---|---|---|
| | | 10 | 60 | 160 | 360 | 660 | 1060 | 1560 |
| Adenosine | Intact (n = 6) | 99.0 ± 0.3 | 96.2 ± 0.7 | 89.7 ± 1.5 | 76.3 ± 3.1 | 60.7 ± 4.2 | 48.5 ± 3.9 | 38.9 ± 2.8 |
| | Denuded (n = 6) | 100.3 ± 0.2 | 100.0 ± 0.4 | 98.9 ± 0.5 | 95.2 ± 1.1 | 87.6 ± 2.3 | 76.6 ± 3.4 | 62.4 ± 4.2 |
| Lidocaine | Intact (n = 6) | 99.7 ± 0.2 | 97.8 ± 0.7 | 96.2 ± 0.6 | 91.7 ± 0.5 | 84.4 ± 1.2 | 76.2 ± 3.5 | 72.2 ± 3.5 |
| | Denuded (n = 6) | 100.0 ± 0.4 | 99.4 ± 0.4 | 96.8 ± 0.7 | 93.4 ± 0.6 | 87.60.8 | 82.4 ± 1.0 | 75.8 ± 2.0 |
| AL | Intact (n = 6) | 97.2 ± 0.5 | 95.8 ± 1.3 | 93.1 ± 1.9 | 79.7 ± 2.3 | 61.8 ± 2.8 | 46.3 ± 2.3 | 36.2 ± 1.3 |
| | Denuded (n = 6) | 99.8 ± 0.1 | 98.5 ± 0.5 | 95.0 ± 1.2 | 84.4 ± 2.0 | 67.5 ± 2.5 | 53.4 ± 2.3 | 42.0 ± 1.3 |

Example 1A

Effect of increasing the concentrations of adenosine (10, 50, 100, 200, 300, 400 and 500 um) on the tension of intact and denuded rat aortic rings precontracted with noradrenalin (FIG. 1).

The effect of increasing the concentrations of adenosine on the tension of intact and denuded rat aortic rings precontracted with norepinephrine are shown in FIG. 1a and Table 1. In intact rat aortic rings, the mean tension in the precontracted state was 3.68±0.11 g (n=6). Expressed as a percent of baseline (3.68 g), the tension values were 99, 96, 89, 76, 61, 48 and 39% for 10, 50, 100, 200, 300, 400 and 500 uM adenosine respectively (Table 1). Muscle tension did not begin to decrease by over 5% relative to the precontracted state until 100 uM adenosine with a relaxation of 10%. At 200, 300, 400 and 500 uM adenosine concentrations, the percent tension decrease was 24, 39, 52 and 61% respectively relative to the baseline norepinephrine precontracted state (Table 2). In denuded aortic rings, the mean tension of the precontracted state was 3.55±0.11 g (n=6). A very different response was found when the endothelium had been removed (FIG. 1). Expressed as a percent of baseline, tension values were 100, 100, 99, 95, 88, 77 and 63% for 10, 50, 100, 200, 300, 400 and 500 uM adenosine respectively (Table 1). In denuded rings the tension did not begin to decrease by over 5% until 300 uM, 400 uM and 500 uM adenosine with a relaxation of 12, 23 and 37% respectively relative to the norepinephrine precontracted state (Table 2).

It can be seen from this data that:
In isolated intact aortic rings, there was no change in adenosine induced relaxations at 10 and 50 uM and only 4% relaxation was found at 100 uM relative to the baseline Nor-adrenalin precontracted state when bathed in 10 mM glucose in Krebs-Henseleit at pH 7.4 37° C. under aerobic conditions (95% $O_2$ & 5% $CO_2$).
Adenosine induced relaxations in intact aortic rings above 5% relative to the baseline Nor-adrenalin precontracted state were only observed at 200 uM (11% relaxation), 300 uM (21% relaxation), 400 uM (34% relaxation) and 500 uM (48% relaxation).
The maximum relaxation in intact aortic rings was found to be at 500 uM adenosine and 48% relative to the baseline Nor-adrenalin precontracted state.
The effect of removing the endothelium was to reduce adenosine's ability to relax the aortic rings at concentrations above 200 uM. The percent adenosine-relaxations in denuded vs intact aortic rings at 200, 300, 400 and 500 uM were 4% vs 11% 5 vs 21, 12% vs 34% and 21 vs 48% respectively. Relaxations over 10% in denuded aortic rings only occurred at 400 uM and relaxation was 35% of the relaxation of the intact aortic rings at the same concentration. Similarly at 500 uM the denuded ring relaxed to 44% of the intact ring at 500 uM.
It is concluded that 1) adenosine can relax intact aortic rings at 200, 300, 400 and 500 uM concentrations, and 2) this relaxation effect is dependent on an intact endothelium. It is concluded that an intact endothelium is a key factor to explain adenosine's ability to relax isolated rat aortic rings precontracted with Nor-adrenalin under aerobic conditions.
Without being bound by any theory or mode of action, one explanation for the endothelium-dependent effect of adenosine is that the endothelium produces a metabolite or factor which relaxes aortic smooth muscle. A candidate for part of the relaxation is nitric oxide, which is normally produced by the healthy endothelium and is known to relax smooth muscle.

Example 1B

Effect of increasing the concentrations of lidocaine on the tension of intact And denuded rat aortic rings precontracted with noradrenalin (FIG. 2)

The effect of increasing the concentrations of lidocaine on the tension of intact and denuded rat aortic rings precontracted with norepinephrine are shown in FIG. 2 and Table 1. The mean tension for intact rings in the precontracted state 3.58±0.07 g (n=6) (Table 1). Expressed as a percent of baseline, tension values were 100, 96, 96, 91, 84, 76 and 72% for 10, 50, 100, 200, 300, 400 and 500 uM lidocaine respectively (Table 1). Muscle tension did not begin to decrease by over 5% relative to the precontracted state until 200 uM lidocaine with a relaxation of 9% and at 300, 400 and 500 uM lidocaine concentrations, the percent tension decrease was 16, 24 and 28% respectively relative to baseline. This tension relaxation profile for lidocaine in intact rings was similar to adenosine alone in denuded rings (ie for adenosine denuded rings the percent fall in tension were 12, 23 and 37% for 300, 400 and 500 uM). In denuded rings the mean tension for the precontracted state was 3.32±0.13 g (n=6) (Table 1). In direct contrast to adenosine, there was little or no difference in lidocaine's tension-relaxation response when the endothelium had been removed (FIG. 1b). Expressed as a percent of the baseline, tension values were 100, 99, 98, 93, 88, 83 and 76% for 10, 50, 100, 200, 300, 400 and 500 uM adenosine respectively (Table 1). Thus, tension did not begin to decrease by over 5% relative to the precontracted state until 200 uM lidocaine where there was 7% relaxation (Table 2). The % relaxation for 300, 400 and 500 uM were 12, 17 and 24% respectively (Table 2). At 500 uM lidocaine, a denuded endothelium led to no significant difference in fall in relaxation compared to the intact endothelium, demonstrating that lidocaine's ability to relax the vessel was endothelium independent.

It can be seen from this data that:
In intact aortic rings, there was no change in lidocaine-induced relaxations at 10 and 50 uM and only 5% relaxation was found at 100 uM relative to the baseline Nor-adrenalin precontracted state when bathed in 10 mM glucose in Krebs-Henseleit at pH 7.4 37° C. under aerobic conditions (95% $O_2$ & 5% $CO_2$). This was similar to the effect of adenosine alone on intact aortic ring preparation over the same concentration range (20 to 100 uM).
Lidocaine induced relaxations in intact aortic rings of 10% and above relative to the baseline Nor-adrenalin precontracted state were observed at 200 uM (10% relaxation), 300 uM (18% relaxation), 400 uM (24% relaxation) and 500 uM (34% relaxation). This was similar to adenosine alone intact aortic ring preparation over the same concentrations (200-500 uM) however the percent relaxations at 300, 400 and 500 uM were less in the lidocaine vs adenosine group ie the lido group generated 14, 30 and 30% of the relaxations of intact adenosine alone at 300, 400 and 500 uM respectively.
The effect of removing the endothelium had little effect on lidocaine's ability to relax the denuded aortic rings implying that lidocaine's effect to relax was mostly via its vascular smooth muscle effect. The percent lidocaine-relaxation in denuded vs intact aortic rings relative to the baseline Noradrenalin contracted state at 200, 300, 400 and 500 uM were 7% vs 10%, 14% vs 18%, 19% vs 24% and 29% vs 34% respectively.

It is concluded that 1) lidocaine relaxes intact isolated aortic rings at higher concentrations (200, 300, 400 and 500 uM), and 2) this effect does not appear to be endothelium dependent. This is in direct contrast to adenosine's effect to relax isolated aortic rings precontracted with Nor-adrenalin under aerobic conditions.

Example 1C

Effect of increasing the concentrations of adenosine and lidocaine solution (eg 10 um adenosine and 10 um lidocaine=10 um conc al, 50 um adenosine and 50 um lidocaine=50 um al and 500 um adenosine and 500 um lidocaine=500 um al) on the tension of intact and denuded rat aortic rings precontracted with noradrenalin.

The effect of increasing the concentrations of adenosine and lidocaine on the tension of intact and denuded rat aortic rings precontracted with norepinephrine is shown in FIG. 3 and Table 1. In the intact rings, the mean tension in the precontracted state was 3.78±0.24 g (n=6). Expressed as a percent of the baseline (3.78 g), tension values were 97, 96, 93, 80, 62, 47 and 36% for 10, 50, 100, 200, 300, 400 and 500 uM adenosine-lidocaine respectively (Table 1). Muscle tension did not begin to decrease by over 5% until 100 uM adenosine-lidocaine with a relaxation of 7%. At 200, 300, 400 and 500 uM adenosine-lidocaine concentrations, the percent tension decrease was 20, 38, 53 and 64% respectively relative to the baseline norepinephrine state (Table 2). In denuded rings, the mean tension in the precontracted state was 3.71±0.19 g (n=6). Expressed as a percent of the baseline, tension values were 100, 99, 95, 86, 68, 54 and 42% for 10, 50, 100, 200, 300, 400 and 500 uM adenosine-lidocaine respectively. Thus, tension did not begin to decrease by over 5% until 200 uM adenosine-lidocaine with a relaxation of 14% (Table 2). At 300, 400 and 500 uM adenosine-lidocaine concentrations, the percent tension decrease was 32, 46 and 58% respectively relative to the baseline (Table 2). The profile of increasing the concentration of AL on relaxation of denuded isolated rat aortic rings was the same as if the intact endothelium was present. No significant differences were found in the AL relaxation profiles between intact and denuded rings when bathed in 10 mM glucose in Krebs-Henseleit at pH 7.4 and 37° C. under aerobic conditions (95% $O_2$ & 5% $CO_2$).

It can be seen from this data that:

for the intact endothelium:

In intact aortic rings, there was little or no change in AL-induced relaxations at 10 and 50 uM and only 4% relaxation was found at 100 uM relative to the baseline Nor-adrenalin precontracted state when bathed in 10 mM glucose in Krebs-Henseleit at pH 7.4 37° C. under aerobic conditions (95% $O_2$ & 5% $CO_2$). This was similar to the effect of adenosine alone and lidocaine alone on intact aortic ring preparation over the same concentration range (10 to 100 uM).

AL solution did not begin to reduce tension in intact aortic rings relative to the baseline precontracted Noradrenalin state until 200, 300, 400 and 500 uM adenosine-lidocaine concentrations with 8, 18, 36 and 48% falls in tension respectively. These concentrations and falls in tension were similar to adenosine alone (% fall in tension for 200, 300, 400 and 500 uM adenosine were 11, 21, 34 and 48%), and greater than lidocaine alone at 400 and 500 uM (lidocaine relaxations were 10%, 18%, 24% and 34% of baseline at 200, 300, 400 and 500 uM). In summary, adenosine-lidocaine had a similar percentage effect to reduce tension (or increase relaxation) as adenosine alone on aortic rings with intact endothelium and about 30% greater falls in tension than lidocaine alone at 400 and 500 uM concentrations for intact and denuded lidocaine preparations.

In denuded aortic rings, there was no difference in the AL-solution induced percentage fall in tension or increased relaxation compared to intact aortic rings when bathed in 10 mM glucose in Krebs-Henseleit at pH 7.4 37° C. under aerobic conditions (95% $O_2$ & 5% $CO_2$). The profile of relaxation was surprising and the same as if the intact endothelium was present.

Example 2

The Effect of Lowering Body Temperature on the Different Resuscitation Strategies The above example is repeated at 35, 33, 20, and 4° C. The formulations are equilibrated with air or aerated or have an oxygen containing perfluorocarbon based, or haemoglobin based substitute present or blood, a blood product or artificial blood. Components may be added to mimic human blood's oxygen transport ability such as Hemopure™, Gelenpol™, Oxygent™, PolyHeme™.

Example 3

Treatment During Surgery

The compositions and methods of the invention can also be used during periods of reduced metabolic activity to reduce damage, such as cell quiescence (medically induced or otherwise). Cardiac surgery is one example. In this example, a known hyperkalemic cardioplegic is used, and the composition of the present invention is administered to reduce tissue damage during the operation.

More specifically, the invention is illustrated by an AL graft storage solution with and without magnesium, dipyridamole and Botulinum Toxin Type A on saphenous vein patency during and following coronary bypass graft surgery. As coronary artery bypass surgery enters its fourth decade of use, an ongoing problem is the early graft occlusion rate of 20% in the first year, or about 480,000 grafts per annum worldwide.

The example's objectives are to (1) examine the antispasm and protective effects of adenosine and lidocaine storage solution mixed with a patient's heparinized blood, with and without magnesium and dipyridamole, on saphenous vein grafts and compare to graft storage in a patient's heparinized blood alone (2) compare the sections of the saphenous vein using histologic analysis immediately after harvesting and before and during 30, 60, 120 and 180 min storage time, and (3) compare the rate of restenosis at 1 month, 6 months and 12 months using non-invasive multi-slice computed tomography (CT) angiography method for visualising and assessing coronary arteries (total vessel diameter, lumen diameter, and wall thickness).

All drugs are obtained from hospital supply houses and approved for clinical use. Adenosine and lidocaine ("AL") are added to 100 ml of the patient's heparinized blood to yield 1 mM final concentrations of each drug. In the magnesium-containing versions, magnesium sulphate is added to a final concentration of 16 mM, and in the dipyridamole-containing versions, the drug is added at 150 uM final concentration. Dipyridamole is a phosphodiesterase inhibitor and a weak antiplatelet agent and known to inhibit the growth of vascular smooth muscle cells, especially venous smooth muscle cells. Kim et al showed that approximately 90% inhibition was achieved at dipyridamole concentrations of 75 microg/mL (0.075/506×1000=0.150 mM). It appears that antiproliferative effects of dipyridamole are sustained for 48 hr after drug exposure of only 15 min.

In Botulinum Toxin experiments diluted amounts of the Botulinum Toxin Type A are added to the AL graft blood storage solution (10 U/ml and 20 U/ml blood ex vivo). The concentration was based on preclinical studies using human saphenous vein rings and rat aortic rings which showed a dose dependent relaxation of vascular smooth muscle. The grafts are kept in the AL storage solution. However before surgical attachment the grafts are removed and washed three times with AL/blood solution alone to remove any residual toxin adhering to the inner wall of the vessel. The temperature of the graft solution will be at 37° C. but may gradually drift down to the temperature of the operating room (22° C.). Special note of the temperature is made because cooling acts as a vasodilator.

Different groups of patients exemplify different embodiments of the invention as follows:

Group 1: Heparinized blood alone;
Group 2: Adenosine and lidocaine (AL) alone (1 mM each)
Group 3: AL+Magnesium Sulphate (16 mM)
Group 4: AL+dipyridamole (150 uM)
Group 5: AL+Botulinum Toxin Type A (20 U/ml)
Group 6: AL+Magnesium+dipyridamole+Botulinum Toxin Type A Sapenous vein harvesting and histological analysis: Patients are anaesthetized using the 'Standard' anaesthetic technique for cardiac surgery. The surgical procedure is the Standard Surgical Technique used by surgeons. Patients have their left or right leg greater saphenous vein harvested by means of the open technique with a traditional longitudinal incision. This is performed by a surgeon's assistant preparing the legs circumferentially and making an incision from the groin to the knee and, if necessary, to below the knee, exposing the entire vein using a continuous incision. The vein is dissected with a combination of Metzenbaum scissors and electrocautery and the vein branches clipped proximally and distally. Once fully dissected, the vein is removed and placed in one of the six storage solutions in 100 ml of the patients heparinized blood. Hemostasis is carried out using electrocautery and surgical clips. The wound is closed in a one-or two-layer fashion with absorbable sutures. The skin layer is closed with surgical staples. The leg is then immediately wrapped with a sterile elastic bandage and remained wrapped for up to 72 hours.

The graft vessel is connected to a pressurized syringe system and tested for any leaks and then any leakages are repaired using sutures or surgical clips. Pressure testing is carried out by connecting the vessel to a syringe system and injecting the appropriate storage solution for each group into the vessel to a pressure of 180 mmHg with one end clamped. After pressure testing the segments or conduits are selected for up to four bypass grafts.

Immediately on harvesting a 0.5 cm segment of the vessel is taken for histological analysis before pressure testing, after pressure testing, and after 30 min and 60 min in the storage solution, and if possible 120 min and 180 min after first placing in storage. The segments are labelled proximal, distal, and centre and placed immediately in a 10% buffered formalin vial. The specimens are fixed and sectioned, processed using light microscopy, and stained with Movat's pentachrome. The slides are evaluated for changes in the intima, media, and adventitia.

Cardioplegia Protocol

The cardioplegia protocol used is as follows.

1) Composition of cardioplegia solution: Induction cardioplegia 20 mM K+ solution (final): BAXTER (Code AHK5524). Each 500 ml Contains: Sodium Chloride BP 4.5 g, Potassium Chloride BP 3 g, Magnesium Chloride BP 2.6 g, Lidocaine HCl BP 250 mg. Before use Sodium Bicarbonate (25 mmol/500 ml) and monosodium Aspartate (14 mmol/500 ml) is added. ~pH 3.7 ~Osmolality 547 mOsm
2) Maintenance cardioplegia 9 mM K+ solution (final): BAXTER (Code AHK5525). Each 500 ml Contains: Sodium Chloride BP 4.5 g, Potassium Chloride BP 1 g, Magnesium Chloride BP 2.6 g. Before use Sodium Bicarbonate (25 mmol/500 ml) and monosodium Aspartate (14 mmol/500 ml) is added. ~pH 3.7~Osmolality 547 mOsm During reanimation, the arrest solution is same as K+ maintenance but the myocardial heart temperature during induction, maintenance and terminal shot are 32 to 38° C. The heart remains arrested at this time.

Hemodynamic and Metabolic Parameters: Routine hemodynamic parameters are measured before, during and following surgery. Echocardiography is used to assess left ventricular wall function. Time to arrest, volumes of cardioplegia administered, myocardial temperature, coronary vascular resistance, incidence of reanimation during arrest, incidence of arrhythmias during arrest, and arterial and coronary sinus lactate, blood gases, pH and ions are measured at 15 min intervals during arrest. After cross-clamp removal, time to first beat, need to electrically cardioconvert, incidence of reperfusion arrhythmias are recorded. CKMB and Troponin I levels are measured before, during and 4, 6 and 12 hours after reanimation. In addition, the use of intra-operative inotropes, blood loss, blood products, pre- and post-operative wall motion and contractility, ejection fraction, ICU and ward stay, incidence of atrial arrhythmias and other post-operative arrhythmias are recorded. Systemic inflammatory markers Interleukin 6 and 8 are also measured during and following surgery.

Assessment of graft patency at 1 month. 6 month and 12 months post-operatively

The rate of restenosis in the grafted vessels can be assessed at 1 month, 6 months and 12 months using non-invasive multi-slice computed tomography (CT) angiography method for visualising and assessing coronary arteries (total vessel diameter, lumen diameter, and wall thickness). Non-invasive examinations are carried out using a scanner with 16 detector rows (Brilliance 16, Philips Medical Systems, Cleveland, Ohio, USA). Contrast flow rate is adapted according to a test bolus acquisition. Pitch settings are modified according to mean heart rate. Coronary lumen diameter is measured using electronic callipers. Hoffmann et al showed that CT angiography using a 16 row multislice detector had very excellent sensitivity (96%) and very good specificity (84%) compared with the invasive "gold standard" for coronary angiography diagnosis of coronary artery disease (Hoffman M H et at Evidence-Based Medicine 2006; 11:24)

Of course, a similar technique could be used but using the newer endoscopic harvesting technique (e.g using Guidant's Vaso View graft harvest system) instead of the more conventional open technique of saphenous graft harvesting described above. Similarly, one could use arterial grafts (eg left or right radial artery) instead of saphenous vein grafts or other artery or venous grafts. It could also be carried out on patients undergoing "on-pump" using cardioplegia as described above or it could be carried out using "off-pump" on the beating heart.

It will be understood that the invention disclosed and defined in this specification extends to all alternative combinations of two or more of the individual features mentioned or evident from the text or drawings. All of these different combinations constitute various alternative aspects of the invention.

I claim:

1. A method of reducing the patency failure rate of a transplanted vasculature graft, the method comprising:
   Prior to transplantation, administering ex vivo to the graft a composition comprising
   i) a potassium channel opener or agonist and/or an adenosine receptor agonist; and
   ii) an anti-arrhythmic agent
   wherein the patency failure rate post operatively of the transplanted vasculature graft is reduced.

2. A method according to claim 1, wherein the composition further includes at least one muscle relaxant.

3. A method according to claim 2, wherein the muscle relaxant is selected from the group consisting of a botulinum toxin, myosin light chain kinase inhibitor, calmodulin blocker, calcium channel blocker, nitric oxide donor, dipyridamole, beta blocker, Na/H inhibitor, high magnesium, opioid, phosphodiesterase inhibitors, alpha-adrenergic receptor antagonists and Rho kinase inhibitors.

4. A method according to claim 3, wherein the phosphodiesterase inhibitor is selected from the group consisting of papaverine, milrinone, theophylline and dipyridamole.

5. A method according to claim 3, wherein the alpha-adrenergic receptor antagonist is phenoxybenzamine.

6. A method according to claim 3, wherein the Rho kinase inhibitor is selected from the group consisting of HA1077 and fausdil.

7. A method according to claim 1, wherein the composition is pre-mixed with the patient's blood.

8. A method according to claim 1, wherein the vasculature is a blood vessel, or a denuded vasculature ring.

9. A method according to claim 8, wherein the blood vessel is a saphenous vein.

10. A method according to claim 1, wherein the composition is administered to the vascular graft during harvesting, storage pending implantation and pressure testing.

11. A method according to claim 1, wherein the composition is administered to the vasculature graft, optionally with at least one smooth muscle relaxant, upon implantation and/or recovery of the vasculature.

12. A method according to claim 1, wherein the composition is also administered systemically or at the site of surgery to the vasculature prior to surgery.

13. A method according to claim 12, wherein the composition is administered as a non-arresting bolus injection or delivered continuously via an intravenous drip.

14. A method according to claim 1, wherein the ex vivo vasculature graft is maintained in a bath of, or having a continuous supply of, the composition.

15. A method according to claim 1, wherein the potassium channel opener or agonist and/or an adenosine receptor agonist is adenosine.

16. A method according to claim 1, wherein the anti-arrhythmic agent is lignocaine.

17. A method according to claim 1, wherein the potassium channel opener or agonist and/or an adenosine receptor agonist is adenosine and the anti-arrhythmic agent is lignocaine.

* * * * *